US011662342B2

(12) United States Patent
Vulto et al.

(10) Patent No.: US 11,662,342 B2
(45) Date of Patent: May 30, 2023

(54) BARRIER FUNCTION MEASUREMENTS

(71) Applicant: MIMETAS B.V., CH Leiden (NL)

(72) Inventors: Paul Vulto, CH Leiden (NL); Sebastiaan Johannes Trietsch, CH Leiden (NL); Henriëtte Leonore Lanz, CH Leiden (NL); Marianne Katharina Vormann, CH Leiden (NL)

(73) Assignee: MIMETAS B.V., CH Leiden (NL)

( * ) Notice: Subject to any disclaimer, the term of this patent is extended or adjusted under 35 U.S.C. 154(b) by 581 days.

(21) Appl. No.: 15/741,076

(22) PCT Filed: Jul. 8, 2016

(86) PCT No.: PCT/NL2016/050502
§ 371 (c)(1),
(2) Date: Dec. 29, 2017

(87) PCT Pub. No.: WO2017/007325
PCT Pub. Date: Jan. 12, 2017

(65) Prior Publication Data
US 2018/0196035 A1 Jul. 12, 2018

(30) Foreign Application Priority Data
Jul. 9, 2015 (NL) ...................................... 2015130

(51) Int. Cl.
G01N 33/50 (2006.01)
G01N 21/64 (2006.01)
G01N 27/447 (2006.01)

(52) U.S. Cl.
CPC ..... *G01N 33/5032* (2013.01); *G01N 21/6428* (2013.01); *G01N 21/6458* (2013.01); *G01N 27/44791* (2013.01); *G01N 33/5008* (2013.01); *G01N 33/5044* (2013.01); *G01N 2021/6441* (2013.01)

(58) Field of Classification Search
None
See application file for complete search history.

(56) References Cited

U.S. PATENT DOCUMENTS

| 10,450,542 B2 | 10/2019 | Vulto et al. |
| 2006/0269909 A1* | 11/2006 | Puddicombe ...... G01N 33/5044 435/4 |
| 2014/0065638 A1 | 3/2014 | Dubrovskyi et al. |

FOREIGN PATENT DOCUMENTS

| WO | 00/28033 | 5/2000 | |
| WO | WO-2012118799 A2 * | 9/2012 | ............ C12M 41/12 |

OTHER PUBLICATIONS

Trietsch et al., Lab Chip, 13, 3548-3554 (Year: 2013).*
Watson et al Gastroenterology 129:902-912 (Year: 2005).*
Bischel et al Biomaterial, 34, 1471e1477 (Year: 2013).*
Hall et al PNAS, 4672-4776 (Year: 1982).*
Jang et al International Conference on Miniaturized Systems for Chemistry and Life Sciences, 15th, Seattle, WA, United States, Oct. 2-6, 2011 vol. 3, 1502-1504, p. 1 (Year: 2012).*
International Search Report, International Patent Application No. PCT/NL2016/050502, dated Sep. 9, 2016.
Van Duinen, V. et al. "Microfluidic 3D cell culture: from tools to tissue models" Current Opinion in Biotechnology, vol. 35, Jun. 19, 2015, pp. 118-126.
Moreno, Edinson L. et al. "Differentiation of neuroepithelial stem cells into functional dopaminergic neurons in 3D microfluidic cell culture" Lab On a Chip, vol. 15, No. 11, Mar. 30, 2015, pp. 2419-2428.
"Transwell Permeable Supports" In: Coming Incorporated: "Transwell Permeable Supports" Dec. 1, 2012, Fisher Scientific, pp. 1-8.
Wilmer, Martijn et al. "Kidney-on-a-Chip Technology for Drug-Induced Nephrotoxicity Screening" Trends in Biotechnology, vol. 34, No. 2, Dec. 18, 2015, pp. 156-170.
Pretot, R. et al. "High throughput in vitro system for nephrotoxicity testing" Toxicology Letters, vol. 238, No. 2, Dec. 1, 2015.
Trietsch, S. et al. "Microfluidic titer plate for stratified 3D cell culture" Lab Chip, 2013, 13, 3548-3554.

* cited by examiner

Primary Examiner — Anoop K Singh
(74) Attorney, Agent, or Firm — Casimir Jones, S.C.; Robert A. Goetz

(57) ABSTRACT

The current invention relates to an improved method for measuring modulating effects of compounds on epithelial cell barrier function. The methods allows for high throughput screening of test compounds individually or in combination. Compounds improving the epithelial barrier function or compounds negatively influencing epithelial barrier function can be analyzed with the method described herein.

17 Claims, 20 Drawing Sheets

LLC-PK1;tube formation in OrganoPlate™

BARRIER FUNCTION MEASUREMENTS

PRIOR ART

Epithelial tissue comprises one of the four basic tissue types (epithelial tissue, connective tissue, muscle tissue, and nervous tissue). Epithelial cells are found in animals (both in vertebrates and in invertebrates) as well as in plants and play a vital role in the physiology of the organism.

Epithelial cells line both the outside and the inside cavities and lumen of bodies. Endothelium (the inner lining of blood vessels, the heart, and lymphatic vessels) and mesothelium (forming the walls of the pericardium, pleurae, and peritoneum) are a specialized form of epithelium.

Epithelial cells form epithelial barriers that act as guards to the internal body. The cells and the barriers they form segregate the internal and external cavities of the body and provide a means for the body to selectively absorb and excrete particular substances. The epithelial barriers and the epithelial cells are for that reason important in a variety of biological processes, such as chemical and nutrient absorption, transcellular transport, detection of sensation, waste excretion, and protecting against microbial infection. All epithelia are usually separated from underlying tissues by an extra cellular fibrous basement membrane.

As an example, epithelia form the structure of the lung, including the alveoli or air sacs, and line most organs, such as the stomach and small intestine, kidney, and pancreas. They also line the esophagus and are found in ducts and glands, like the bile duct and salivary glands. They form taste buds, line the nose, the ear and the eye and the skin.

The endothelium is the thin layer of endothelial cells that lines the interior surface of blood vessels and lymphatic vessels, forming an interface between circulating blood or lymph in the lumen and the rest of the vessel wall, such as the blood-brain barrier.

Mesothelial cells form a monolayer of specialized pavement-like cells that line the body's serous cavities and internal organs. The primary function of this layer, termed the mesothelium, is to provide a slippery, non-adhesive and protective surface. However, mesothelial cells play other pivotal roles involving transport of fluid and cells across the serosal cavities, antigen presentation, inflammation and tissue repair, coagulation and fibrinolysis and tumor cell adhesion.

Epithelial cells are characterized by a number of distinguishable characteristics. Epithelial cells are bound together in sheets of tissue called epithelia. These sheets are held together through several types of interactions, including tight junctions, adherens, desmosomes, and gap junctions. Tight junctions act as the delineation between the apical (upper) and basal (lower) regions of an epithelial cell in conjunction with polarization between the two regions. Epithelium is supported on the basal side by a basement membrane called the basal lamina.

As mentioned, one distinguishing feature is the formation of tight junctions that segregate the plasma membrane of the polarized epithelial cell into an apical and a basolateral portion. The apical portion of the cell is the exposed, or top, portion of the cell when oriented in a cell monolayer grown in vitro, for example on a tissue culture plate. In the context of an epithelial cell sheet in the body, the apical surface would be exposed to the lumen lined by the epithelium. The basolateral surface of the cell is composed of the bottom, or basal, portion and the side, or lateral, portions. In the context of a cell grown on a tissue culture plate, the basolateral membrane of the cell is the portion of the cell contacting the tissue culture plate and the lateral portion of the cell situated below the tight junctions. In the context of an epithelial cell sheet in the body, the basolateral surface of the cell would be exposed to the internal portion of the body lined by the epithelium. Various proteins localize specifically to the apical or basolateral membrane.

Given the importance it is not surprising that epithelial cells (including endothelial cell and mesothelial cell) are widely used to study a variety of biological processes. The cells are well suited for studies in fields like molecular cell biology, (microbial) pathogenesis, pharmacology, and toxicology.

Numerous model systems have been developed to study epithelial cells and barrier function. Studying epithelial cells normally requires the ability to access or modify the culture medium that is in contact with the apical or basolateral surfaces of the epithelial cells. Since standard tissue culture devices do not allow for this sort of manipulation specialized cell culture devices have been developed. The primary device used in most in vitro model systems is a permeable tissue culture plate insert, such as a Transwell® (Corning, Inc., Lowell, Mass.). These devices provide an artificial permeable growth support that can be inserted into a well of a tissue culture plate. By culturing a polarized cell monolayer across the surface of the permeable growth support it will function as a selective barrier to separate the apical and basolateral chambers of the tissue culture well.

Such model systems play a vital role in the development of new medicines, understanding various diseases and understanding the toxic effects of agents.

For example, during the drug development process, potential therapeutic agents or drug candidates must be demonstrated to be both safe and effective for their intended use prior to obtaining approval and subsequent commercialization. Various drugs are known to negatively modulate epithelial barrier functions (see, e.g., Youmba et al. J Pediatr Gastroenterol Nutr 2012; 54:463-70). On the other hand, compounds that modulate the barrier function of epithelial cells, for example by temporarily opening the barrier may be useful to improve drug delivery to the systemic circulation and to organs (Deli, Biochimica et Biophysica Acta—Biomembranes 1788 (4) 2009, 892-910). Likewise, temporarily opening the blood brain barrier may be useful in delivery of drugs to the brain. Furthermore, such systems are important to understand the effect of all kinds of compounds, including those found in food, cosmetics, and beverages, and bacteria, on the barrier function. For example, *Clostridium difficile* toxins disrupt epithelial barrier function by altering membrane microdomain localization of tight junction proteins (Nusrat et al. Infect Immun. 2001 March; 69(3):1329-36), whereas other components may be increasing or supplementing epithelial barrier function.

While current epithelial cell model systems are useful for drug discovery, working with the cells in these systems has turned out to be difficult due to the highly uniform cell monolayers needed for this work. The experimental work requires choosing the correct cell type, producing multiple uniform cell monolayers, and ensuring cell monolayer integrity is sufficient to conduct the experiments. Furthermore, all of these must be well-established to allow for repeated production of experimentally acceptable results. These difficulties can make developing a desirable epithelial cell model system a daunting process, requiring months or years of work.

Accordingly, there is great interest in the development of new high throughput screening assays which are capable of rapidly providing data on epithelial barrier function for a large number of different compounds. It is therefore an object of the present invention to provide an improved assay which results in better understanding of the effects of compounds on epithelial barrier function.

DESCRIPTION OF THE INVENTION

Definitions

Various terms relating to the methods, compositions, uses and other aspects of the present invention are used throughout the specification and claims. Such terms are to be given their ordinary meaning in the art to which the invention pertains, unless otherwise indicated. Other specifically defined terms are to be construed in a manner consistent with the definition provided herein. Although any methods and materials similar or equivalent to those described herein can be used in the practice for testing of the present invention, the preferred materials and methods are described herein "A," "an," and "the": these singular form terms include plural referents unless the content clearly dictates otherwise. Thus, for example, reference to "a cell" includes a combination of two or more cells, and the like.

"About" and "approximately": these terms, when referring to a measurable value such as an amount, a temporal duration, and the like, is meant to encompass variations of ±20% or ±10%, more preferably ±5%, even more preferably ±1%, and still more preferably ±0.1% from the specified value, as such variations are appropriate to perform the disclosed methods.

"Comprising": this term is construed as being inclusive and open ended, and not exclusive. Specifically, the term and variations thereof mean the specified features, steps or components are included. These terms are not to be interpreted to exclude the presence of other features, steps or components.

"Exemplary": this terms means "serving as an example, instance, or illustration," and should not be construed as excluding other configurations disclosed herein.

"Microfluidic system": this term refers to a device, or a fluidic component of a device, that is configured for containing, flowing, processing, or otherwise manipulating small volumes of liquid, such as in the sub-picoliter to sub-milliliter, or milliliter range. In some example embodiments, the maximal cross-sectional dimension of a microfluidic feature, such as a microfluidic channel, may be less than 1 mm, less than 500 microns, less than 100 microns, less than 50 microns, or less than 25 microns.

"Luminescent probe": this term refers to any probe or molecule that emits light. Types of luminescence include bioluminescence, chemiluminescence, electrochemiluminescence, electroluminescence, and photoluminescence. The probe may be luminescent on its own, luminescence may the consequence of a chemical or enzymatic reaction involving the luminescent probe or may be the consequence of excitation of the probe with light, followed by light emission by the probe at a different wave length. The latter is also known as fluorescence. Fluorescence is a type of luminescence and the result of absorption of photons, so it is a type of photoluminescence. Within the context of the current invention, also included under the term "luminescent probe" are colorimetric probes.

Probe: this terms refers to a system, composition or molecule, the presence or absence of which can be detected (qualitative and/or quantitative), e.g. a detectable molecule, marker or substance. Within the context of the current invention, the probe is used to measure the epithelial barrier function. By providing a probe and measuring the signal created by the probe at the apical, basolateral or both sides, a measure of the epithelial barrier function is obtained. For example, if a probe is provided at one side of the cell layer, appearance of the probe on the other side indicates the probe has crossed the layer of cells. Increased rate of appearance indicates increased "leakage" over the layer of cells. In other words, a probe, within the context of the current invention, refers to something that is detectable; e.g. provides a signal or can be induced to provide a signal. The skilled person understand that, within the context of the current invention, this might be any type of substance, molecule or system that allows detection thereof, for example, in at the apical, basolateral side of the cells of the epithelial layer, or even in these cells. For example, based on monitoring the distribution of the probe, or the rate of redistribution of the detectable probe, epithelial barrier function may be determined. For example, as can be witnessed from the prior art, a probe may also be referred to as a (detectable) marker, substance, marker substance, reagent, label, or molecule. Examples of probes that can easily de detected and determined include, but are not limited to luminescent substances and compounds, dyes, fluorophores, radioactive compounds, sensor molecules and the like. However also other molecules, the presence of which can be detected at the apical and/or basolateral side (or within the cells) is envisaged. The skilled person understands that the detection of the signal provided by the probe will depend on the type of prove or marker substance used. For example, in case the probe is a fluorescent probe, fluorescence may be determined. For example in case the probe is a radioactive probe, radioactivity may be determined. For example, in case the probe is an enzymatic substrate, the probe may be determined by performing an enzymatic assay on a sample. The skilled person understands that the signal provided by the probe will depend on the type of probe used. The skilled person understands that the current disclosure is not in particularly limited by the type of probe used as long as it may be suitably used within the context of the current invention.

Preferably, the probe is an optical probe, i.e. the signal created or provided by the probe can be detected using optic means (for example measuring absorption, fluoresce, or chemiluminescence). Well-known probes that allow for optical monitoring include, but are not limited to luminescent probes (including fluorescent probes), dyes, and colorimetric probes. The probe may also consist of a sensor molecule or composition provided on one side of the cells (apical or basolateral) and a further molecule or composition provided on the other side of the cells, wherein the sensor molecule of composition is detectable, preferably optically, when it is comes into contact with the further molecule or composition. The detected signal indicates that the further molecule or composition has crossed the cells, indicative for the epithelial barrier function.

DETAILED DESCRIPTION OF THE INVENTION

Figure 1:
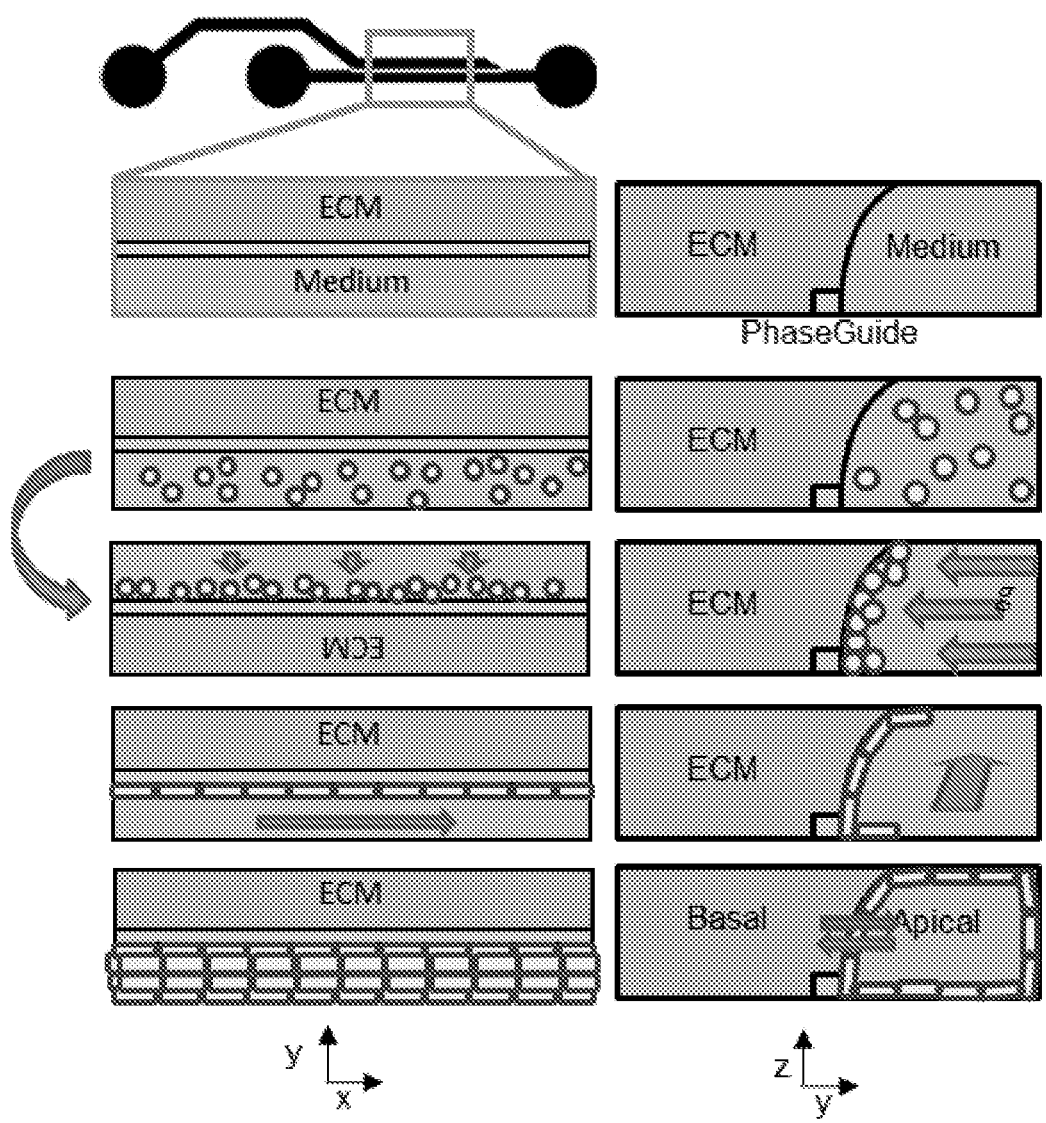
FIG. 1A-1B shows seeding of a barrier against an Extra-Cellular Matrix in the microfluidic platform: A) Schematic of seeding cells against an ExtraCellular Matrix (ECM). B) Example of the formation of a tubular structure in the medium perfusion channel
Figure 1:
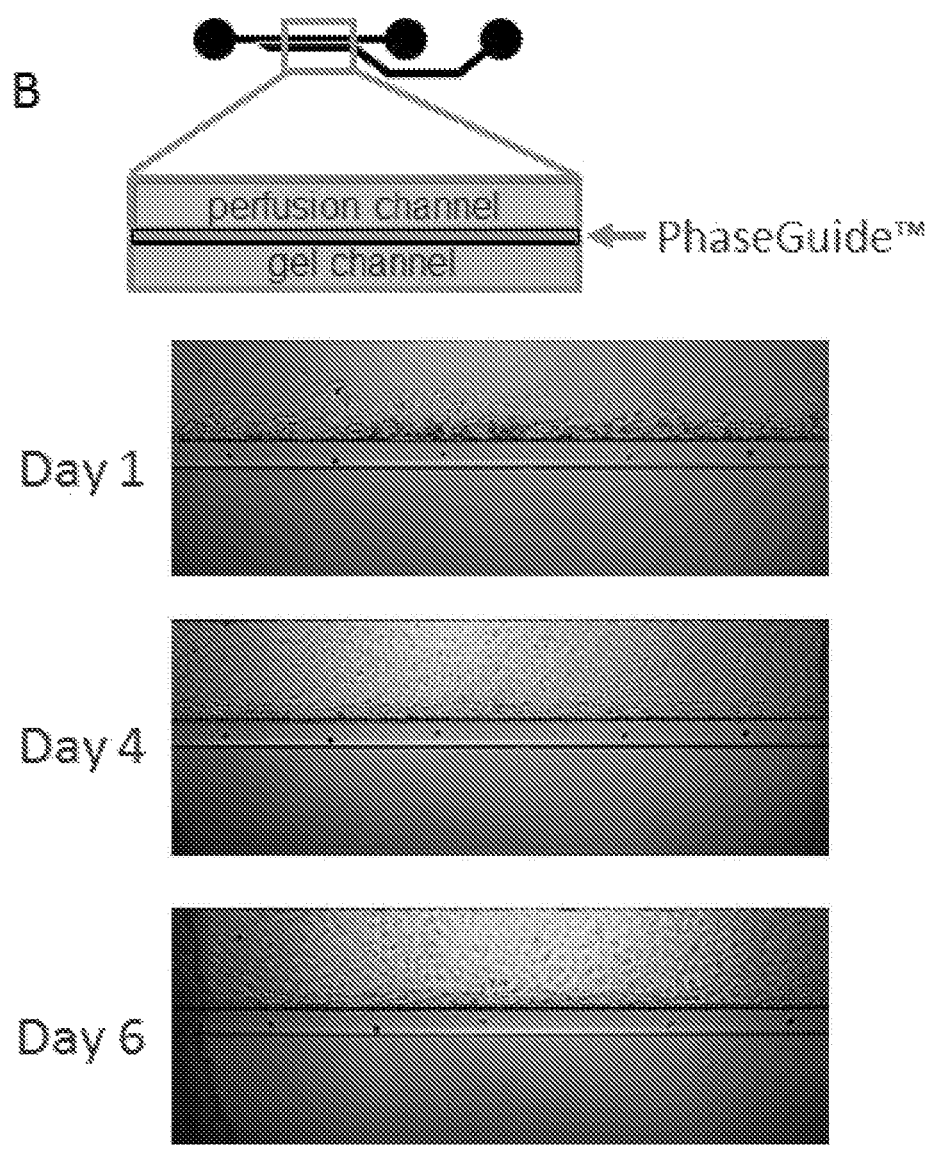

Disclosed is an in-vitro method for determining the modulating effect of a test compound on the epithelial barrier function. Epithelial barriers are not fixed, static structures. They can become leakier or less leaky in response to various different stimuli. Disease processes and agents may make barrier linings leakier, and the site of such leak is often at, for example, the tight junctions (Mullin et al. (2005) Drug Discov. Today, 10:395-408).

Because permeability is a dynamic phenomenon, increasing to one stimulus and/or decreasing to another, the basal state of epithelial barrier in any given epithelial tissue can generally be modulated to become tighter or modulated to become leakier.

In general, increased leakage is deleterious, while decreased leakage works either physiologically or immunologically to the organism's benefit.

The method of the invention now makes it possible to determine, measure, analyze, predict or establish the negative or positive effect of a compound on the epithelial barrier function. In some embodiments, the methods make it possible to gain detailed insight in the modulating effect of the compound on the epithelial barrier function. The methods make it possible to compare different compounds, compound concentrations or different conditions on its effect on the epithelial barrier function. In particular the method allows studying or establishing the modulating effect of a compound on the epithelial barrier function as a function of time. The method of the invention makes it possible to distinguish between the various leakage phenomena occurring in a cell layer (or monolayer), for example disruption of tight junctions, appearance of pin-holes in the cell layer/membrane, leakage from the sides due to incomplete monolayer attachment; all of which is not possible with methods in the art, for example with Transwell systems. Importantly, the method of the invention allows for real-time monitoring of the modulation effects on the epithelial barrier function; real-time monitoring enables determination of time to leak; this is a much better value for the effect a compound has on the epithelial barrier function of the cell layer than fluorescence intensity, since the latter also comprises aspects such as applied pressure due to liquid levels.

The method of the invention is easier in use, as the experiment can be followed by real-time imaging, while with Transwell systems aliquots have to be taken from the wells over time and measured separately from the Transwell system. Moreover, since the method of the invention deals with small volumes in the microfluidic channels, even the slightest changes in fluorescence can be observed; this in contrast to Transwell systems, where low amounts of fluorescence disappear in the large fluid quantities.

In some embodiments, the results obtained with the method of the invention are indicative for the toxic effects of the compound. In some embodiments, the results obtained with the method of the invention are indicative for the usefulness of the tested compound to temporarily open up the epithelial barrier (i.e. to temporarily reduce the barrier function). In some embodiments, the results obtained with the method of the invention are indicative for the mechanism (how and how quickly) by which a compound may exert its toxic effects. In some embodiments, the results obtained with the method of the invention are indicative for the barrier function improving effects of the test compound.

The method is reliable, straightforward and highly reproducible, making it in particular suitable for screening purposes. In addition, the method of the inventions allows to quickly identify whether the results obtained are representative for the effect of the compound on the barrier function or whether the results should be rejected as false due to experimental flaws. The method of the invention allows for real-time measurements.

The method relies on measuring the movement (passive or active; for example in practice overpressure may be applied to increase the influx of compounds through epithelial barrier to the other side; the gel allow for interstitial flow through the gel) of a probe (or, in case the probe comprises of a sensor and further molecule or composition as described herein, movement of the further molecule or composition) from one side (apical or basolateral) side of an epithelial layer to the other side of the epithelial layer of cells cultivated in a microfluidic system. The measurement is performed over time, and in the absence of or presence of a test compound. The rate of transport, or the amount of transport over time, or, in particular, the time during which a certain level (relative or absolute) of transport is accomplished, provides new insights in the effect of the tested compound on the epithelial cells used in the method.

The in-vitro method for determining the modulating effect of a test compound on the epithelial barrier function is described as the method comprising the following stages or steps:

a) providing a microfluidic system comprising multiple hollow microfluidic channels, wherein the channel is filled at least in part by a gel;

b) introducing epithelial cells in to the microfluidic channels and allowing the epithelial cells to contact the gel;

c) culturing the epithelial cells that were introduced in to the microfluidic channels, thereby allowing the cells to form on the gel a layer of cells with an apical and a basolateral side, preferably thereby allowing the cells to form a tubular structure with an apical and a basolateral side in the microfluidic channel;

d) providing to the epithelial cells in the microfluidic channel a probe and the test compound, wherein the probe and the test compound are, independently, provided to the apical side, to the basolateral side or to both the apical and basolateral side;

e) determining at various time points the signal provided or created by the probe in the microfluidic channel or in the gel, or both in the microfluidic channel and in the gel.

The absolute values, the change in the values, or the ratio of the values of the signal determined in step e), in particular over various time points, were surprisingly found to be highly reproducible indications for the effect of the compound on the barrier function of the epithelial cells. The values can, for example, be used to express the toxic effect of the compound on an epithelial cell, or on the epithelial barrier.

In a first step, there is provided a microfluidic system that comprises multiple hollow microfluidic channels. Obviously, the microfluidic system needs to be suitable for cultivating epithelial cells. In addition, the microfluidic systems must provide access to either the apical or the basolateral, but in a preferred embodiment, to both the apical and basolateral side of epithelial cells once cultivated in the microfluidic system.

Microfluidic systems suitable for cultivating cells are known to the skilled person and refer to a device, or a fluidic component of a device, that is configured for containing, flowing, processing, or otherwise manipulating small volumes of liquid, such as in the sub-picoliter to sub-milliliter, or milliliter range.

The microfluidic systems used in the method of the invention are suitable for in vitro cell culture support, and may provide active support to living cells by a system of microfluidic channels that provide flow, for example by passive means like passive leveling or by using active pumps, such as syringe pumps and the like. Flow pertains to a support system for living cells where fluid is delivered to or extracted from some or all of the channels by use of an external positive or negative pressure source, for example a pressure pump, a pressurized tank, a vacuum pump, or the like. Active support relates to a support system for living cells where some or all of the channels receive active microfluidic flow. An active microfluidic system may be contrasted to a system using passive microfluidic flow, wherein fluid circulation is impelled by naturally occurring mechanisms such as gravity, capillary action, surface tension or the like to drive the flow. The microfluidic system in the method of the invention may provide for flow or operate without flow.

The microfluidic system used may provide flow to the cell cultivated in the microfluidic channels wherein the cells reside through the system of microfluidic channels, thereby providing a suitable fluid environment to the cells.

The microfluidic system may include channels of substantially even caliber, or may include channels with varying calibers, including constrictions and dilatations, as required by the fluid flow dynamics.

The microfluidic system used in the method of the invention is not in particular limited to any specific microfluidic system. Exemplary microfluidic devices are described in S. J. Trietsch, G. D. Israëls, J. Joore, T. Hankemeier, P. Vulto, Microfluidic titer plate for stratified 3D cell culture, Lab Chip 2013, vol. 13, no. 18, pp. 3548-3554, Edinson Lucumi Moreno, Siham Hachi, Kathrin Hemmer, Sebastiaan J. Trietsch, Aidos S. Baumuratov, Thomas Hankemeier, Paul Vulto, Jens C. Schwamborn and Ronan M. T. Fleming, Differentiation of neuroepithelial stem cells into functional dopaminergic neurons in 3D microfluidic cell culture, Lab Chip, Vol. 15, No. 11, pp. 2419-2428, in WO2012120102 in WO2014038943, in Mu et al, Lab on a Chip, 2013, 13, 1612-1618, or in Jang et al, integr biol, 2013, 5, 1119. However, the latter two do not allow for high-throughput screening and are less preferred.

The device described in WO2012120102, for example, comprises a hollow volume that (a) is internally divided into at least first, second and third sub-volumes by at least two phaseguides formed inside the volume and (b) includes parts that are relatively upstream and relatively downstream when judged with reference to the movement of a meniscus or a bulk liquid in the volume. The device including at least first, second and third fluid conduits connected to permit fluid communication between the upstream exterior of the volume and a respective said sub-volume; and at least one further conduit connected to permit fluid communication between the downstream exterior of the volume and a said sub-volume. The first said sub-volume may contain cells supported in or by a gel or gel-like substance; and the second sub-volume communicates with the first sub-volume so as to permit transport of substances between the first and second sub-volumes and containing at least one gel or gel-like substance. In some embodiments described therein the third sub-volume communicates with at least the first sub-volume so as to permit transport of substances between the first and third sub-volumes, and wherein the third sub-volume contains a perfusate.

Preferred microfluidic plates or systems comprise a plurality of microfluidic networks and inlets providing access to the microfluidic networks. Each microfluidic network comprises a capillary pressure barrier. Each inlet is formed by an inlet chamber having a bottom surface.

In practice, a fluid dispenser having a dispensing part with an end for dispensing fluid is used for inserting liquids and/or gels and/or gel precursors into the microfluidic network, thereby stopping or patterning at least one of the liquids/gels/gel precursors by means of a capillary pressure barrier. The microfluidic plate may be used for studying fluids or their contents or assessing the interaction between fluids or their contents.

The capillary pressure barrier can for example divide a microfluidic chamber of the microfluidic network into a first chamber part and a second chamber part. A liquid, gel or gel precursor with life based particles such as cells may be discharged by the dispensing part of the fluid dispenser in the inlet. Said liquid or gel (precursor) will flow from the inlet into the first chamber part of the microfluidic chamber and is stopped, its advancement controlled or patterned due to the presence of a capillary pressure barrier. The liquid or gel (precursor) may be transported through the microfluidic network by capillary forces, by gravity or other actuating forces.

An example of the use of such a capillary pressure barrier is to selectively fill a microfluidic network with a first fluid, such as for instance a gel. The extent to which a microfluidic network is filled with said first fluid is determined by a capillary pressure barrier that halts advancement of the fluid in the network. Upon gelation the remainder of the microfluidic network may be filled with a second fluid such that exchange between the two fluids occurs or a reaction between the fluids or their components occurs. An example thereof shown ins the 3D culture of cells in an extracellular matrix gel that is flanked by a medium perfusion flow. This is extensively described in S. J. Trietsch, G. D. Israëls, J. Joore, T. Hankemeier, P. Vulto, Microfluidic titer plate for stratified 3D cell culture, Lab Chip 2013, vol. 13, no. 18, pp. 3548-3554.

Other examples of use a capillary pressure barriers are given in C. Phurimsak, E. Yildirim, M. D. Tarn, S. J. Trietsch, T. Hankemeier, N. Pamme, P. Vulto, Phaseguide assisted liquid lamination for magnetic particle-based assays, Lab Chip, 2014, vol. 14, no. 13, pp. 2334-2343, P. Vulto, G. Dame, U. Maier, S. Makohliso, S. Podszun, P. Zahn, G. A. Urban, A microfluidic approach for high efficiency extraction of low molecular weight RNA, Lab Chip, 2010, vol. 10, no. 5, pp. 610-6, Edinson Lucumi Moreno, Siham Hachi, Kathrin Hemmer, Sebastiaan J. Trietsch, Aidos S. Baumuratov, Thomas Hankemeier, Paul Vulto, Jens C. Schwamborn and Ronan M. T. Fleming, Differentiation of neuroepithelial stem cells into functional dopaminergic neurons in 3D microfluidic cell culture, Lab Chip, Vol. 15, No. 11, pp. 2419-2428, US020070280856A1, US020040241051A1, US000004761381A, US000006271040B1, WO2006074665, U.S. Pat. No. 6,601, 613B2, U.S. Pat. No. 6,637,463B1. The capillary pressure barrier may be any one of a hydrophobic patch, or stripe, a less hydrophilic patch or stripe with respect to the ulterior network material, a channel widening, one or more pillars or posts lined in a channel or chamber, a groove in the channel or chamber substrate, a protrusion of the material into the chamber volume and the like.

Particular preferred are Mimetas' OrganoPlates (http://mimetas.com/products.php).

These are microfluidics-based culture plates that enable culturing and screening of a wide range of physiologically relevant organ and tissue models.

The microfluidic network of such microfluidic system comprises in general a channel, chamber, multiple channels or chambers or a combination thereof, wherein at least one dimension of at least one channel or chamber is often, and preferred less than one millimeter.

A microfluidic network is typically constructed as a horizontally layered setup comprising a bottom substrate, a layer comprising the microfluidic network and a top substrate. The microfluidic layer may also be patterned into or onto either or both of the top and bottom substrates. The microfluidic network comprises polymer or glass top and bottom substrates. The microfluidic network may be constructed either by etching the network into either substrate or by patterned in a polymer layer on top of either substrate. In a particular embodiment, at least one of the top or bottom substrate is constructed out of glass or a hydrophilic polymer, such that fluid transport may be achieved by capillary forces only. The microfluidic plate (system) could be constructed using photolithography techniques, hot-embossing techniques, soft embossing techniques, etching techniques, replication moulding or injection moulding techniques.

The wall of the channels may be of any type of material, including but not limited to glass, polymers such as polysterene, PMMA, COC, elastomers such as silicone rubbers, polydimethylsiloxane, ceramics, metals.

The channel is filled at least in part by a gel, preferably a hydrogel. The skilled person understands that different types of gels are suitable and may be used in the context of the current invention, including those routinely used in cell culture techniques, and as long as the gel allows for cultivation of the epithelial cells within the context of the current invention. Indeed experiments show that different gels, such as those specifically mentioned herein, may be used. Indeed the skilled person will have no difficulty choosing a suitable gel. The gel can be provided to the channel as described above. After the gel is provided, it is caused to gelate, prior to introduction of a further fluid. This fluid is typically a growth medium that provides nutrients and oxygen. Via this fluid, cells can be introduced thereby depositing them against the gel and allowing the cells to form a layer of cells. Upon bringing these cells in culture, they typically form a tube that can be perfused with a flow through the lumen of the tube. Thus, gel is provided to the channel such that after gelation, the epithelial cells can be introduced in the channel by means of a medium, for example a culture medium, allowing the cells to contact the cells and to form on the gel a layer of cells (e.g. a tubules/vessel), thereby creating an apical and basolateral side.

For example, a gel precursor (typically from an extracellular matrix (ECM) gel, such as collagen, fibrinogen, fibronectin, basement membrane extract such as Matrigel or synthetic gels) may be introduced into an inlet of the microfluidic plate with a pipette (typically a repeating pipette such as the Eppendorf Multipette® M4 (Eppendorf AG, Germany, catalogue number 4982 000.012) in combination with Eppendorf Combitips Advanced® (Eppendorf AG, Germany, catalogue number 0030 089.405). The gel precursor may further contain cells yielding a cell suspension, but cells may also be provided afterwards. The gel precursor is released into the inlet of the microfluidic plate. The gel precursor is transported into the microfluidic network by capillary forces, potentially assisted by gravity. The gel is subsequently halted by a phaseguide, which is essentially a capillary pressure barrier that spans the complete width of a microfluidic chamber. The gel precursor is caused to gelate, prior to introduction of a second fluid. This second fluid is typically a growth medium that provides nutrients and oxygen. In the case of a flow, the growth medium may also remove or dilute waste metabolites as produced by the cells.

In a similar manner as the above example, cells can be introduced in the second fluid, thereby depositing them against the gel. Upon bringing these cells in culture, they typically form a tube that can be perfused with a flow through the lumen of the tube In yet another example, multiple gels could be patterned adjacent to one another. Multiple gels can be patterned by injecting gel precursors, halting advancement of the precursors by a capillary pressure barrier and causing the precursors to gelate in different parts of the network sequentially. Suspension of a first cell type in a first gel precursor, followed by a second cell type in a second gel precursor results in a so-called stratified co-culture, in which cell types cultured adjacent to one another.

The gel preferably is in contact with/deposited against the channel wall.

Gels are defined as a substantially dilute cross-linked system, which exhibits no flow when in the steady-state. A gel is often a non-fluid colloidal network or polymer network that is expanded throughout its whole volume by a fluid. A hydrogel, or aqua gel, is a gel in which the swelling agent is water. Within the context of the method of the invention, the gel material may be a water-containing gel that is preferably insoluble in water but comprises water so as to have a two- or three-dimensional support structure. In the present invention, the gel used allows for diffusion of a substance, in particular of the probe (or further compound as defined herein) and/or the test compound (see below) in and over said gel. Examples include Matrigel and collagen-based gels The gel used in the invention is not particularly limited as far as the layer has the above properties and allows for the forming of a layer of epithelial cells on the gel (detailed below). Commonly used gels include gels from biological origin comprising collagen, laminin, fibronectin, fibrinogen, Matrigel and/or agarose, and synthetic gels based on several scaffolds such as PEG (polyethylene glycols), peptides, PLLA (poly-L-lactide), PLGA (poly(lactic-co-glycolic acid).

Several techniques can be used to pattern the gel, i.e. to fill part of the microfluidic channel with the gel, including but not limited to lithographic patterning of photocurable gels, capillary force based patterning using e.g. pillars, hydrophobic patches or phaseguides, and selective deposition.

To the microfluidic system comprising the hollow microfluidic channels and wherein in such channel is filled at least in part with the gel, epithelial cells are provided. The cells may be introduced in the channels by any suitable means as long as the cells can contact the gel in the microfluidic channel.

Within the context of the current invention, the term epithelial cells also refers to epithelial cells, endothelial cells or mesothelial cells, the latter two being special forms of epithelial cells. The number of cells introduced in a channel should allow for the cells to form a layer of cells on the gel after cultivation in a suitable medium, and depends on the type of cell used, the type of gel used and the type of medium used. The skilled person is well aware what conditions are required to meet these requirements or how to establish these.

Once the cells have been introduced in a microfluidic channel, the cells are allowed to grow, expand or divide in order to allow the cells to form on the gel a layer of cells with an apical and a basolateral side. Within the context of the current invention, the apical side of the cell is the side facing the interior of the microfluidic channel whereas the basolateral side is the side of the cell that is facing the gel (or that is in contact with the gel). Within the context of the current invention also the side faced by the basolateral side of the cell is denoted as basolateral, whereas the side faced by the apical side of the cell is denoted as apical.

In a preferred embodiment, the cells are cultivated for a period sufficient for the cells to form a tubular structure in the microfluidic channel, again defining an apical and a basolateral side as defined herein.

The cells are cultivated in a medium and under conditions suitable for the particular cell selected, and using methodology well known to the skilled person.

With respect to the forming of a layer of cells with an apical and a basolateral side, in a preferred embodiment said layer is confluent. Within the context of the current invention, confluence is expressed relative to the surface of the gel material in the microfluidic channel. Confluence is the term commonly used as an estimate of the number of adherent cells in the microfluidic device, referring to the proportion of the surface which is covered by cells. For example, 50 percent confluence means that roughly half of the surface of the gel is covered. When a layer is said to be confluent, about 100 percent of the surface of the gel is covered by the cells, and no more room is left for the cells to grow as a monolayer.

When the cell layer, for example the monolayer, is confluent with respect to the part that is in contact with the gel, it was found that the monolayer is leak tight. Indeed epithelial barrier function can within the context of the method disclosed herein be defined based on the rate by which a probe (or part of a probe system) diffuses or drifts from one side of the epithelial cell layer (apical or basolateral) to the other side of the epithelial cell layer (basolateral, respectively apical). With a fully functional epithelial barrier function this rate will be close to zero whereas in the absence of any epithelial barrier function the rate will be close to or be the rate in the given system in absence of any cells. The skilled person knows that under given circumstance the interstitial flow due to a difference in apical and basal pressure will affect the transport and may thus be taken into account when performing experiments. Any value between these extremes indicates a varying level of epithelial barrier function, with values close to zero being indicative of a more functional epithelial barrier function.

In other words, under these conditions the probe (or part of the probe system), when for example added at the apical side, will not or only very limitedly move or diffuse or drift from the apical side towards the basolateral side of the cells, indicative of a fully functional epithelial barrier. The probe, when given apical, will not accumulate in the gel.

Within the context of the current invention, the epithelial cell layer may be considered leak tight when less than about 10%, preferably less than about 5%, even more preferably less than about 1% of the signal appears on the side (for example apical) opposite to the side where the probe (or the further compound in case of the use of a sensor; as defined herein) was provided (in this example, basolateral) within 5, 10, 20 or 30 minutes after addition. In a preferred embodiment, an epithelial layer is considered leak tight when less than 1% of the signal appears for a period of 5 minutes. This number will depend in part on the probe used as well as the type of cells used.

However it was surprisingly found that for the method of the invention it is not required that the layer needs to be largely leak-tight with respect to the probe for at least the part that is in contact with the gel. In practice a certain level of leakiness may be allowed from the start of the experiment. In other words, it is allowable with the method of the invention that at the start of the experiment the probe, and in the absence of a test compound, to a certain extent moves from one side to the other side as the consequence of a non-leak-tight epithelial layer, for example as a consequence of reduced confluence of the cells in the layer with respect to the gel.

In fact, in some embodiment such non-leak-tight epithelial cells are preferred as this allows to study or screen compounds with respect to their epithelial barrier enhancing properties, for example by measuring the reduction in the rate of diffusion/movement of the probe from one side to the other side over time.

The extent by which the epithelial barrier function may thus be disrupted at the start of the experiment largely depends on the goal of the experiment. Obviously diffusion of the probe (which in the context of the invention, and in every embodiment herein also comprises the movement of the further molecule or composition in the case a sensor system is used as a probe; as defined herein) from one side to the other side should not be equal to the rate in the absence of any cells in the given system. In some embodiments, preferably movement or diffusion at the beginning of the experiments, and before any test compound is provided to the cells is at most 50%, 40%, 20%, 10%, 5%, 2%, 1%, 0.5% or less of the movement/diffusion rate observed in the same system in absence of any cells.

With respect to the tubular structure that in some embodiment may be obtained, preferably the tubular structure is confluent for at least the part of the tubular structure that is localized relative to the gel, or that is in contact with the gel.

Based on the disclosure herein the skilled person will understand what can still be accepted with respect to the non-leak-tightness of the layer of cells that is formed on the gel. At the same time, the method thus allows to quickly determine or establish whether a layer of cells can be suitably used or should be rejected because of reduced or even absent epithelial barrier function.

After the cells were allowed to form a layer of cells and therewith with an apical and a basolateral side, the cells in the microfluidic channels are provided with a probe. The probe may be provided either to the apical medium or to the basolateral medium, to both the apical and basolateral medium. The latter may for example involve the addition of two different and distinguishable probes. Preferably the probe is an optical probe; i.e. may be monitored with optical mean. Preferably the optical probe is a luminescent probe. As described herein, a luminescent probe includes any probe that emits light on its own, or that emits or creates lights as the consequence of a chemical of enzymatic reaction involving the luminescent probe, or emits light upon excitation (fluorescence). In case, for example the luminescent probes require co-factors or substrates in order to emit light, such co-factors or substrates may be added to the medium, either at the apical side, the basolateral side or both. It should be noted that when using co-factors or substrates, the probe does not need to actually emit the light itself, but should be a vital part of the luminogenic process, e.g. a fluorescent part of the co-factor could be unquenched in the presence of the luminescent probe.

If the cofactors or substrates are selectively provided at the opposite side of the cell layer to the probe, the measure of diffused or drifted probe will be the absolute amount of light generated as opposed to the ratio between apical and basal light, as no light will be generated at the side without cofactor or substrate/pct The cells are also provided with the compound to be tested. The compound, independently of the probe, is provided to the apical side, the basolateral side or to both the apical and basolateral side of the cells. The compound (test agent) may be added concurrently with the probe, or before or after the probe is provided to the cells. The compound may be an agent to be tested for ability to modulate epithelial barrier function. Modulation of epithelial barrier function may involve increased epithelial barrier function, decreased barrier function, or supplemented epithelial barrier function (wherein the compound does not increase epithelial barrier function per se, but for example act as a coating agent for an epithelial cell layer and thereby supplementing such epithelial barrier function). The activity of the compound with respect to epithelial barrier function may be already known or unknown. Compounds to be tested may include but are not limited to antibodies, small molecule inhibitors, drugs, natural or synthetic mucosal protective agents, cytokines, growth factors, antioxidants, antiproteases, natural or synthetic epithelial secretions and mimetics of surfactants or any other intervention.

As indicated above, of particular interest are compounds that will or are suspected to increase, supplement or decrease epithelial barrier function.

During a next stage of the method of the invention, the signal created or provided by the probe or probe system is determined at various points in time. The signal may be determined at the apical side, at the basolateral side, or both at the apical and the basolateral side. For example, where the probe is provided at the basolateral side, movement of the probe to the apical side may be measured by measuring the signal at the apical side, where an increase in signal indicates diffusion to the apical side. However diffusion or drift to, in this example, the apical side may in some embodiments also be determined by measuring the signal at the basolateral side, wherein a decrease in the signal indicates diffusion to the apical side. The signal may also be measured in both compartments, i.e. in both the apical or basolateral medium or gel. As will be explained in detail below, measuring the signal at the basolateral side may comprise measuring the signal in the gel, but may also comprise measuring the signal in medium that has access to the basolateral gel, and wherein the probe may accumulate from the gel. Within the context of the invention, measuring the basolateral signal in the gel thus comprises both measuring in the gel, or in the said medium, or both.

The method used to measure the signal depend on the particular probe used in the method of the invention. Depending on the probe used, the skilled person knows what method to use. For example, in case of fluorescent probes, fluorescence of the probe is determined using any suitable means.

Preferably the probe is an optical probe, preferably an luminescent probe, preferably a fluorescent probe. It is noted that the probe, optical probe, luminescent probe, fluorescent probe, may also comprise of a sensor molecule or composition that provides a signal once contacted by a further molecule or composition. By providing the sensor on one side and the further molecule or composition on the other side, leakage can be detected by measuring the signal created/provided by the sensor when contacted by the further molecule or composition.

The signal is preferably determined at more than one time point. In practice, at the first time point the signal in absence of the test compound may be determined in order to obtain a first control value. In the practice of the invention, and at the same time as testing the effect of a test compound on epithelial barrier function on one or more channels, one or more channels comprising a layer of cells will be used as control, i.e. wherein the signal provided by the probe will be determined or measured over time and under the same conditions but in absence of a or the test compound. Indeed, and applicable to all embodiments of the invention, the medium can be changed after treatment to modify the duration of exposure of the culture to the substance. In addition, normally but not necessarily, one runs controls or standards together with the test culture to determine whether there has been a problem with the incubation conditions. Controls are cell cultures which are identical to that used for testing except they are not disrupted and are not treated with the substance to be tested.

The results that are obtained may be used in different ways. For example, the modulating effect of a compound on the epithelial barrier function may be expressed as the absolute or relative change in the signal at the apical side, the basolateral side or both over time. Alternatively the results may be compared to control experiments, performed under the same conditions but in the absence of the test compound. Also, various concentrations of a test compound may be compared (for example, 1, 2, 3, 4, 5 . . . 10 different concentrations). It is also possible to express the signal at the apical side relative to the basolateral side, and the other way around (but absolute values as well as relative changes). The data may also be expressed as change (absolute, relative) in signal per time unit.

The rate at which a probe diffuses or drifts across the epithelial cell layer can be further analyzed to yield the apparent permeability ($P_{app}$) of the cell layer for the particular probe. This value is a generally accepted descriptor of the barrier function of epithelial layers. To calculate this value one can, for example monitor the diffusion or drift of the probe through the cell layer against the supporting gel and correct it for the diffusion or drift that is observed in control devices with gel without cells. A formula that can be used for such a calculation can be $$P_{app} = \frac{\Delta C_{receiver}}{\Delta t} \frac{V_{receiver}}{A \times C_{donor, initial}} \left(\frac{cm}{s}\right)$$

Where t is time, A is the area of the cell layer that the probe can cross, $V_{receiver}$ is the volume of the part of the device that the probe diffuses or drifts towards, $C_{receiver}$ is the probe concentration in the part of the device that the probe diffuses or drifts towards and $C_{donor, initial}$ is the initial concentration of the probe in the compartment that the probe diffuses out of.

To separate the permeability of the cell layer form that of the gel one can use the formula:

$$\frac{1}{P_{app\ determined}} = \frac{1}{P_{monolayer}} + \frac{1}{P_{cell\ free}}$$

In which $P_{app\ determined}$ is the $P_{app}$ of the cells on top of the gel, $P_{monolayer}$ is the $P_{app}$ layer of cells and $P_{cell\ free}$ is the $P_{app}$ of the control devices with gel without cells. This formula can be rearranged to $$P_{monolayer} = \frac{P_{cell\ free} \times P_{app\ determined}}{P_{cell\ free} - P_{app\ determined}}$$

To use this method, the drift or diffusion of probe should be monitored for a length of time in which the increase of signal is still approximately linear. For example, an experiment could comprise the exposure of different monolayers to different compounds or concentrations of compounds for different amounts of time. After this exposure the probe can be added to the monolayers and control devices, and the drift of probe monitored for between 5 and 60 minutes. Applying the above formulas will then yield the apparent permeability of the cell monolayers after the different treatments.

In some embodiments, different compounds are tested in sequence in the same channel. In such embodiment cells in a particular channel are first contacted with a first compound, and after some time an additional compound to be tested is added or cells are first contacted with a first compound, after which the first compound is removed and a second compound to be tested in provided to the same cells in the channel.

The method of the invention also allows to test mixtures of compound. In such embodiment a mixture of compounds is provided to a microfluidic channel comprising the cells.

In some embodiments a continuous flow of media may be provided alongside the gel opposite from the cell monolayer and alongside the monolayer. Such a flow can remove any probe that diffuses or drifts completely across the gel. In a preferred embodiment, the flow and volume behind the gel is such, that the concentration of the probe dissolved in it never reaches significant levels, effectively creating a constant sink situation. In a further embodiment, a continuous flow is also provided on the opposite side of the cell layer. Preferably the flow and volume of the fluid containing the probe is such that the concentration of the probe never decreases significantly due to diffusion or drift across the cell layer, effectively creating a constant source. If both the constant source and constant sink are present, the fact that the diffusion or drift through the gel is constant, the only factor affecting the concentration of probe inside the gel is the diffusion or drift across the cell layer. This enables direct estimation of the flux of probe, and thus the barrier function of the cell layer, by only measuring the concentration of probe in the gel region. As opposed to some other embodiments where the increase of probe concentration over time is measured, this embodiment using constant flow to achieve a constant source and sink allows direct and dynamic measurement of the barrier function at any time point.

In a preferred embodiment various test compounds or mixtures of test compounds, for example a mixtures of 2, 3, 4, 5, . . . 10 different test compounds, preferably at different concentrations may be compared. In particular the latter may be of importance for applications in the pharmacology, nutritional and/or cosmetics fields. As an example, patients nowadays often take different medications at the same time or during the day. It may be important to understand the effect of such combinations on epithelial barrier function. For example, in asthma, on one hand medication may be given to improve or supplement epithelial barrier function in the lungs, whereas on the other hand such patient may receive medication that, unintentionally, annul or counter act such improvement.

In general, an increase in the signal provided or created by a given probe at the side opposite to the side to which the probe was added is indicative for a not fully leak-tight epithelial barrier. The stronger the increase, the less the epithelial barrier function is.

With the method of the invention it has now become possible to obtain more detailed information with respect to the effect of a compound on epithelial barrier function. One reason is that the epithelial cells used in the method of the invention represent are a more representative model to the in vivo state in comparison to methods in the art that mainly rely on the use of permeable tissue culture plate inserts, such as a Transwell® (Corning, Inc., Lowell, Mass.; such insert provides an artificial permeable growth support that can be inserted into a well of a tissue culture plate). A second reason is that the signals can be monitored in real-time, as many time points, and for layers of cells in one experiment. A third reason is that with the method of the invention it becomes possible to identify the characteristics of the mechanism by which a compound modulates the epithelial barrier function. For example, the method of the invention makes it possible to establish if the effect of a test compound is immediately observable after providing the compound to the cells, or if there is lag time between the moment the compound is added and modulation of the barrier function occurs. In addition, the method of the invention can be used to establish more subtle effects of a compound on the cells than a live/dead effect. Measuring epithelial barrier function, i.e. boundary integrity, upon compound addition, gives a value of toxicity that is much more subtle than such live/dead assessment. A test compound might, for example, hamper the tight junctions of a cell layer, or inhibit or reduce the self-regenerative capacity of the layer of cells or the tubular structure, as well as kill cells (but not all of them).

A problem that is solved with the method of the invention is that live/dead analysis is difficult if not impossible to quantify when dealing with flow systems, i.e. with microfluidic systems as used in the method of the invention. In the presence of flow dead cells are flushed away, while at the same time the epithelial barrier has a certain regenerative capacity that makes up for the killing of cells. Measuring the barrier integrity, thus gives a clear indication of loss of function, regenerative capacity or cell death that is straightforward to measure using the method of invention.

In practice it was also found, that a toxic effect affecting boundary integrity is not an instantaneous event, but might happen at a certain point in time. It was also found that the time-point at which boundary integrity was compromised relates to the concentration of compound added. In fact, it is believed by the inventors that the concentration of compound affects cell death versus regenerative capacity ratio, or tight junctions as a function of time. The time between compound administration and the point at which the adverse effect of barrier integrity loss can be measured, is thus an important measure to the toxic effect of a compound at a certain concentration. In a highly preferred embodiment of the method of the invention, the method therefor further comprises the step of:

f) determining from the signals obtained in step e) the time that passed from the time point of providing the test compound and/or the probe to the epithelial cells to the time point a predetermined value or predetermined change in value of the fluorescence in the microfluidic channel and/or in the gel is reached, or to the time point a predetermined value or a predetermined change in the value of the ratio of fluorescence in the microfluidic channel (apical side) and the gel (basolateral side) is reached.

In this preferred embodiment, the time between providing the test compound and/or the probe is provided to the epithelial cells and the moment that a certain predetermined value or change in the value of the signal is reached either at the apical side, the basolateral side or both the apical and basolateral side is calculated for the test compound at the concentration tested.

The values thus obtained is a measure of the "time-to-leak" and may be compared between different test conditions, for example by comparing the time from adding the test compound and/or probe to the predetermined value for different tested concentrations of the test compound. As explained, such data is an important measure to the toxic effect of a compound at a certain concentration and made possible for the first time with the method of the invention. The predetermined value will depend on the type of cells used and may be empirically determined. For example the predetermined value may be based on the results obtained with a reference compound, or may be based on the results obtained with controls. For example, when for a reference compound A it is known that at a given concentration a certain ratio between the signal at the apical side and at the basolateral side (for example the ratio of the signal in the medium in the channel and the signal in the gel) is reached after, for example 20 minutes, such ratio may be used as a benchmark for testing the modulating effect of other compounds. In addition the time-to-leak for different concentrations of the test compound can be compared with the method of the invention.

Indeed in some embodiments of the method of the invention, the method is performed for more than one concentration of the test compound, preferably wherein step f) is determined for more than one concentration of the test compound. In these embodiments, various concentrations of a test compound may be compared (for example, 1, 2, 3, 4, 5 ... 10 different concentrations). In addition, and in some embodiments various test compounds or mixtures of test compounds, for example a mixtures of 2, 3, 4, 5, ... 10 different test compounds, preferably at different concentrations may be compared.

Also provided is a method of the invention wherein the effect of a test compound on the epithelial barrier function is determined, preferably concurrently, i.e. within the same experiment, in more than one of the microfluidic channels comprising the cultivated epithelial cells, preferably wherein the effect of more than one concentration of the test compound on the epithelial barrier function is concurrently, that is to say, within one and the same experiment, determined. In practice the signal provided in different channels are measured sequentially in such embodiment wherein the effect of a test compound on the epithelial barrier function is determined, preferably concurrently.

With the method of the invention is has become possible to determine the modulating effect of test compounds in one and the same experiment over time and under different conditions. In some embodiments, therefore, the test compound is provided to more than one microfluidic channel (or channel network) in the same experiment. In some embodiments the concentration of the test compound provided to the different channels is the same, in other embodiments, the concentration of the test compound that is provided to the different channels varies per channel. The method of the invention allows for determining, in one experiment, and thus using epithelial cell layers that were all obtained under the same conditions, the effect of a compound on epithelial barrier function at a concentration over time, of the effect of different concentrations over time, obtained from one or more channels comprising a layer of cells. This allows providing of good quality and representative data.

The skilled person will understand that, depending on the desires of the user, the method of the invention may also be used to test different compounds, at one or different concentrations, over time in one and the same experiment (i.e. concurrently). In some embodiments there is provided therefore for a method of the invention wherein, independently, the effect of more than one test compound on the epithelial barrier function is concurrently, that is to say, in the same experiment, determined in at least part of the multiple microfluidic channels (or channel network) comprising the cultivated epithelial cells.

In such an embodiment, cells grown under identical conditions but in different channels, preferably in the same microfluidic systems, are treated with different test compounds (or, in given cases, mixtures of test compounds, or cells in one channel exposed sequentially to different compounds) and the effects determined over time, and in preferred embodiments at different concentrations.

As described herein, although preferably the layer of cells that is in contact with the gel is leak-tight, i.e. the probe does not, or only to a limited extent diffuse or move from one side to the other side (e.g. from the apical to the basolateral side), this is not necessary for the method of the invention. In fact in some embodiments a certain (limited) level of diffusion is preferable as it allows to study whether a compound can modulate the epithelial barrier function by restoring it (as measured by a decrease in diffusion of the probe). Alternatively, there is provided for a method of the invention wherein prior to or concurrently with step d) the barrier function is disrupted.

According to the invention, a (preferably repeatable) disruption may be produced in the layer of (preferably confluent) cells. One method of forming the disruption is by freezing a part of the cells in the cell layer, of otherwise destruction such part, for example using laser light, certain compounds, ultrasonic or acoustic signals, bubble in- or explosions, abrasive beads, or by adding a compound that was shown to reproducibly disrupt the cell layer, either based on own experiments or based on literature.

Next, the test compound is added to initiate the test. Normally, treatment is just after disruption of the culture, but occasionally the culture is treated with the material to be tested before disruption to determine a particular type of effect. For purpose of this procedure, treatment can be any means of exposing the culture to the compound being tested. The specific method of treatment varies depending on the properties of the substance.

A determination of the level at which the substance inhibits, stimulates or otherwise effects closure of the disruption is achieved by comparing the effects of different amounts of the substance, for example using serial dilutions, as described herein.

In some embodiments the test compound is provided to the cells before the probe is provided to the cell layer. In some embodiments, the test compound is provided to the cells after the probe is provided to the cell layer. In some embodiments the test compound is provided at the same time as the probe is provided to the cell layer. As indicated before, preferably the cells are in the form of a tubules or vessel. Such tubules or vessel represents a more physiologically relevant state when dealing with blood or lymph vessels or tubules like the proximal tubule. The reason is that the mechanical cues that cells experience are similar to those in vivo, and they have a clear luminal side through which they may experience flow (but not strictly necessary). Although both the test compound and the probe may be provided to the same side (i.e. the apical side, the basolateral side or both), they may also be provided to different sides (for example the test compound is provided at the basolateral side whereas the compound to be tested in provided to the apical side, or if so desired at the apical and the basolateral side). There is therefor provided a method of the invention, wherein the test compound is provided to the cells before, after or at the same time with the probe. The time between providing the test compound and the probe may vary depending on the experimental set-up. In some embodiments the time period is less than one, five, ten or thirty minutes. In other embodiment the time period is about 10, 30, 60 seconds, or about 5, 10, 30, 60 minutes, or about 1, 2, 6, 12, 24 or 48 hours.

In some embodiments more than one type of probe is provided to the cells. In some embodiments, the probe is provided after the test compound is provided. Is some embodiments a further probe is provided after a first probe and the test compound are provided, for example, some time after the test compound and the first probe were provided to the cells. Such embodiment may for example be used in experiments aimed at first detecting disruption or repair of the epithelial cell layer (including tubules) with a first probe, followed by determining repair of disruption by a second probe, for example after removal of the first test compound, or after a period of exposure to the test compound (e.g. the measure adaptation or the like by the cells).

In some embodiments, more than one test compound is provided to the cells. Mixtures of compounds may be tested, for example in order to determine if one compound in the test mixture interacts with another compound in the mixture, thereby modulating its effects on the epithelial barrier function. Test compounds in a mixture may also act synergistically on the barrier function or may antagonize each other.

Indeed, although the layer of cells does not necessarily has to be leak-tight, and some diffusion of the probe is allowable at the initiation of the experiment (i.e. when the test compound is added), in a preferred embodiment, the cell layer is leak-tight, that is to say, virtually no, or substantially no diffusion of the probe if observed when provided to the cells, in absence of the test compound. Therefore the invention also provides for a method of the invention wherein the cells cultured in step c) form a monolayer, preferably wherein the monolayer does substantially not allow the probe to diffuse from the apical side to the basolateral side and/or from the apical side to the basolateral side. Within the context of the current invention, the epithelial cell layer may be considered leak tight when less than about 10%, preferably less than about 5%, even more preferably less than about 1%, 0.1%, 0.01% of the signal diffuses from one side (for example apical) to another side (in this example, basolateral) within 5, 10, 20 or 30 minutes after addition. This number will depend in part on the probe used as well as the type of cells used. In some embodiments, preferably diffusion or drift at the beginning of the experiments, and before any test compound is provided to the cells is at most 50%, 40%, 20%, 10%, 5%, 2%, 1%, 0.5% or less of the diffusion rate observed in the same system in absence of any cells. In practice, often a (slight) over pressure of the fluid on the side of the probe is applied, in order to speed up "compound leakage" and thus have a clearer signal. This is possible as there is interstitial flow present in the gel. For instance, one may add 100 microliter medium comprising the test compound and probe to the reservoirs that communicate with the lumen side of the cell layer/tubule and only 20 microliter medium to the reservoirs that communicate to the other side of the tubule. Thus a slight overpressure is created on the luminal side, giving a clear signal when disruption of the barrier occurs.

As disclosed herein in step e) comprises the determination at various time points the signal provided by the probe in the microfluidic channel or in the gel, or both in the microfluidic channel and in the gel. The skilled person understands that the determination at various time points indicates that at least two time points (during the experiment/method) the probe (also referred to as marker substance) is determined in, for example, the apical side and/or basolateral side (or even with the cells) of the cells. In other words, the probe (the signal provided by the probe) is determined over time, and at least at two different moments. The skilled person understands that, depending on for example, the purpose of the experiment or assay, he may vary with the moment of the first measurement/determination, the time between two measurements, the total number of measurements, the period of one measurement, the total length of the measurement and so on. For example he may perform a first measurement before addition of a test compound, 1 second after the provision of the test compounds, 1 hour, 12 hours, 1 day, 3 days and so on. For example he may measure every 1 second, every 1 minute, and every 1 hour, every 6 hours, every day, every week or every month, and anything between and above that, if so desired. For example he may measure for less than a second or more than a second, less or more than a minute, less or more than an hour, less or more than 6 hours, less or more than a day, week or month. For example the time between two measurements may be less or more than a second or less or more than a minute, less or more than an hour, less or more than 6 hours, less or more than a day, week or month and so on.

Also provided is the method of the invention wherein two successive time points in step e) are within 1 second to 24 hours of each other. The signal provided by the probe is, in the method of the invention, determined at various time points. The period between two time points may vary. For example, the period between a first and second time point may be 5 seconds, whereas the time period between the second and third time point is 10 minutes. In principle the time period between two time points may be any suitable period. However, in practice, the time between the time points should be taken as such as to obtain reliable data for each time point. For example, during the period between the first view time point may be relatively short, whereas the time period between later time points may be relative long. However, if, from the experimental data obtained it appears that a change in epithelial barrier function appears to occur in an interval wherein the period between two time points is relatively long, the experiment may be repeated with a shorter time period in said interval in order to more precisely determine the changes in epithelial barrier function. Typically a period between two time points may be between 1 second and 24 hours, for example 1 second and 20 minutes of each other. It is again noted that not each period between two time points should be the same or should be within the given range.

Also provided is a method of the invention wherein the various time points in step e) are within a period of between, and inclusive, 10 minutes and 4 weeks (e.g. 28 days). Although the experiment may be continued and measurement may be taken at many different time points, it was found that in general the modulating effect of a compound on epithelial barrier function, in particular toxic effects, occur rather quickly after addition of the test compound. In some embodiments therefore, the total period wherein at different time point the signal is determined may be between, and inclusive, 10 minutes and 4 weeks (e.g. 28 days).

In that respect it is to be noted that the first measurement not necessarily has to be performed immediately after the chemical compound and/or the probe is provided to the cells. As indicated, the test compound may, for example, be provided to the cells several minutes or hours before the probe is provided, for example in order to allow the test compound to exert its action in relationship to the epithelial barrier function. In such an embodiment, the first measurement may be performed several hours after addition of the test compound and may continue, for example for 10 minutes to 4 weeks (e.g. 28 days).

Also provided is the method of the invention, wherein adjacent to the gel a further channel is present that is in contact with the gel, wherein said channel is not in direct contact with the microfluidic channel comprising the cultivated epithelial cells.

Said further channel is in direct contact with the gel, but is separated with the microfluidic channel comprising the cultivated epithelial cells by said gel (and the cells forming the monolayer on said gel. The further channel is thus part of the basolateral side and may be used, as described herein, to measure signal provided by the probe or to add test compounds or other compounds to the basolateral side of the cells. Test compounds and probes can diffuse through the gel in order to reach the basolateral side of the cells, or can diffuse through the gel in order to reach the liquid in the further channel.

Also provided is the method of above, wherein in said further channel a flow is present that removes the probe from the gel, and preferably wherein the determining of the signal provided by the probe in step e) in the gel comprises measuring the signal in the flow present in said further channel, and/or in the gel.

In general, and for the various embodiments described herein, measurement can be performed in the microfluidic device in several ways. For example, there may be applied 1) a constant flow in the channel, i.e. at the side, where the probe is provided (donor side). In such embodiment, this causes a constant source of the probe at, for example the basolateral or apical side. Measurements are in such embodiments preferably done based on the signals obtained on the other side.

2) Alternatively, no use is made of a flow at the donor side, i.e. wherein there is no constant source of probe. In such static embodiment, diffusion of the probe to the other side (i.e. to the basolateral side/gel/further channel or to the apical side/medium in the microfluidic channel) leads to reduction on the level of the probe in the channel to which the probe was provided, which has to be taken into account when interpreting the obtained data.

3) There may be applied no flow in the acceptor side (i.e. the apical or basolateral side to which the probe may diffuse, when added to the opposite side (apical to basolateral; basolateral to apical)). This will result in accumulation of the probe at such side over time, and is thus the integral of leakage over the measured time interval. This embodiment may in particular be used when the basolateral side (i.e. the gel) is used as the acceptor side.

4) There may be applied a constant flow at the acceptor side. This does not cause accumulation at the acceptor side (and possible redistribution of the probe to the donor side). In that case the leakage per time point, or time leakage per time point can be determined in the acceptor side (for example in the gel, in combination with the further channel as discussed below).

In a preferred embodiment, a flow is applied to either the donor side or the acceptor side, or both. In another preferred embodiment, a flow is applied at one side and not the other side. In a preferred embodiment, a flow is applied at the basolateral side. In another embodiment, a flow is applied at the apical side. In an embodiment, a flow is applied at the donor side only. In a further embodiment, the test compound is added to the side where no flow is applied. In a further embodiment, the test compound is added to the side where flow is applied. In a further embodiment, when the test compound is added to the side where flow is applied, the flow provides for a constant concentration at the side where the compound is provided. In another embodiment, when the test compound is added to the side were flow is applied, after the initial provision of the test compound, the flow does not, or in a lower concentration, comprise the test compound; causing a decrease in the concentration of the test compound at the side where the compound is provided. In an even further embodiment, after the initial provision of the test compound, the flow does comprise varying concentrations or increasing concentrations of the compound, thus causing varying concentrations or increased concentration of the test compound at the side where the test compound is provided.

The method of the invention does not only allow for determining the modulating effect of a test compound or different test compounds over time, and/or at different concentrations, but also allows for testing in a repeatable way, the modulating effects of a test compound or of different test compounds, at one or more concentrations, over time, for different epithelial cells or for different compositions of epithelial cell layers. Thus, also provided is a method of the invention wherein in step b) different types of epithelial cells are introduced in the same microfluidic channel and/or wherein in step b) different microfluidic channels are provided with different types of epithelial cells. The skilled person is well aware how to prepare a microfluidic device comprising more than one type of epithelial cells. This embodiment allows detecting, for example, epithelial cell type specific effects of a test compound.

The gel used in the method of the invention may be any suitable gel as long as the provided epithelial cell type may form on the gel a layer of cells with an apical and a basolateral side. For example, the gel may comprise synthetic polymers, a natural polymers, or biopolymers, including agarose, gelatin, dextran, chitosan, silica gel and the like.

In a preferred embodiment however, the gel comprises one or more growth and/or differentiation substrates, such as collagen, collagen I, collagen IV, fibronectin, laminin, vitronectin, D-lysine, entactin, heparan sulfide proteoglycans, similar tissue culture substrates, or combinations thereof.

In another embodiment the gel comprises a basement membrane extract, human or animal tissue or cell culture-derived extracellular matrices, animal tissue-derived extracellular matrices, synthetic extracellular matrices, hydrogels, collagen, soft agar, egg white and commercially available products such as Matrigel. Basement membranes are thin extracellular matrices which underlie epithelial cells in vivo and are comprised of extracellular matrices, such a protein and proteoglycans. Although an epithelial cell layer, multilayer or monolayer, prevents the invasion of an exogenous material from the external world as a barrier, a basement membrane itself also acts as a physical barrier. Thus, epithelial cells comprising an epithelial tissue collaborate with a basement membrane to form a solid barrier and to protect the internal vital activity.

They are composed of collagen IV, laminin, entactin, heparan sulfide proteoglycans and numerous other minor components (Quaranta et al, Curr. Opin. Cell Biol. 6, 674-681, 1994). These components alone as well as the intact basement membranes are biologically active and promote cell adhesion, migration and, in many cases growth and differentiation. An example of a gel based on basement membranes is termed Matrigel (U.S. Pat. No. 4,829,000). This material is very biologically active in vitro as a substratum for epithelial cells.

Many different suitable gels for use in the method of the invention are commercially available, and include but are not limited to those comprising Matrigel rgf, BME1, BME1rgf, BME2, BME2rgf, BME3 (all Matrigel variants) Collagen I, Collagen IV, mixtures of Collagen I and IV, or mixtures of Collagen I and IV, and Collagen II and III), puramatrix, hydrogels, Cell-Tak™, Collagen I, Collagen IV, Matrigel® Matrix, Fibronectin, Gelatin, Laminin, Osteopontin, Poly-Lysine (PDL, PLL), PDL/LM and PLO/LM, PuraMatrix® or Vitronectin.

In one preferred embodiment, the matrix components are obtained as the commercially available Corning® MATRIGEL® Matrix (Corning, N.Y. 14831, USA)

MATRIGEL® Matrix is extracted from the Engelbreth-Holm-Swarm ("EHS") mouse tumor, a tumor rich in basement membrane. The major matrix components are laminin, collagen IV, entactin, and heparin sulfate proteoglycan ("HSPG"). The matrix also contains growth factors, matrix metalloproteinases (collegenases), and other proteinases (plasminogen activators), as well as some as yet undefined extracellular matrix components. At room temperature, MATRIGEL® Matrix gels to form a reconstituted basement membrane.

Thus provided in a preferred embodiment of the method of the invention is a method wherein the gel comprises a basement membrane extract, an extracellular matrix component, collagen, collagen I, collagen IV, fibronectin, laminin, vitronectin, D-lysine, entactin, heparan sulfide proteoglycans or combinations thereof, and preferably wherein the gel is in direct contact with the cell layer without any physical membrane separating the two.

In contrast to methods in the art, the current invention does not rely on the use of tissue culture inserts having a permeable support, such as the Transwell® insert already described herein. Such inserts are normally made of polycarbonate, polyester, polytetrafluoroethylene, polystyrene, or polyethylene terephthalate, as well as other similar substances. Such support therewith form diffusion barriers as the material from which these inserts are prepared are inaccessible for, for example the probe used in the method of the invention. It was surprisingly found that by using a gel in the method of the invention that allows the gel to be in direct contact with the cell layer and does not form a physical and impermeable membrane between the layer of cells and the gel, the negative effects of the presence of such impermeable and non-natural layer are circumvented. It was found this in particular provides for more sensitive measurement of the modulating effect of a compound on the epithelial barrier function when compared to assays relying on the use of such support or inserts comprising impermeable material to provide for the support and therewith creating for at least part of the cells a physical barrier.

The method of the invention can be used for any type of epithelial cell (including endothelial cells and mesothelial cells), as can be witnessed from the examples herein, showing various types and sorts of epithelial cells, and that can be cultivated in the channels of the microfluidic system. The cells may be animal epithelial cells, animal epithelial cell line cells, animal epithelial primary cells, mammalian epithelial cells, mammalian epithelial cell line cells, mammalian epithelial primary cells, human epithelial cells, human epithelial cell line cells, or human epithelial primary cells. Examples of epithelial cells are encompassed by the term as used herein include but are not limited to prostate cells, mammary cells, hepatocytes, pancreatic islet cells including beta cells, pulmonary epithelial cells, kidney cells, bladder cells, stomach epithelial cells, large and small intestinal epithelial cells, urethral epithelial cells, testicular epithelial cells, ovarian epithelial cells, cervical epithelial cells, thyroid cells, parathyroid cells, adrenal cells, thymus cells, gall bladder cells, pituitary cells. As described herein, the cells can be from any animal, including but not limited to any mammal, such as mouse, rat, canine, feline, bovine, equine, porcine, non-human and human primates. Mammalian cells particularly suitable in the present media include epithelial cells of human origin, which may be primary cells derived from a tissues such as but not limited to mammary glands, prostate glands, liver, pancreas, kidney, bronchi and trachea. In addition, transformed cells or established cell lines can also be used. The cells used in the present invention may be normal, healthy cells that are not diseased or not genetically altered, or the cells may be diseased or genetically altered.

Within the context of the invention, a cell line refers to continuously growing or immortalized cells. Sometimes also referred to as "immortalized cell line", a cell line is a population of cells from a multicellular organism which would normally not proliferate indefinitely but, due to mutation, have evaded normal cellular senescence and instead can keep undergoing division. The term is well-known to the skilled person. A cell line cell thus denotes a cell that belongs to such cell line. Examples of epithelial cells lines suitable for the method of the invention include LLC-PK1 (porcine kidney cells) cells, Madin-Darby Canine Kidney cells like MDCKI cells, MDCKII cells, A549, HMEC-1, ECV304, EaHy926, Caco-2 cells, CEBBe1 cells, HT-29 cells, T84 cells, and SK-CO15 cells, or derivative cells such as epithelial cells genetically engineered, and many others.

Within the context of the invention, primary cells are cells taken directly from living tissue (e.g. biopsy material) and are established for growth in vitro. These cells have undergone very few population doublings and are therefore more representative of the main functional component of the tissue from which they are derived in comparison to continuous (tumor or artificially immortalized) cell lines thus representing a more representative model to the in vivo state.

Both primary epithelial cells and epithelial cell line cells are obtainable from various commercial sources, including from the American Type Culture Collection (ATTC).

Also provided is a method of any of the previous claims wherein the determining of the signal provided by the probe in step e) comprises measuring using an imaging device, a microscope, an automated microscope, a high content imager, a plate reader, or a multimode reader.

Suitable methods and devices for measuring the signal are well known to the skilled person, who has no problem to select a suitable method. High-content imaging devices may for example be obtained from Molecular Devices (Sunnyvale, USA) or others.

Also provided is a method of the invention wherein the microfluidic device provides an uninterrupted optical path to the microfluidic channel and/or to the gel and/or to the further channel. This will allow for the uninterrupted measurement of the signal either at the apical, basolateral or both sides.

The modulating effect may be either an effect that increases the epithelial barrier function of the cell layer or may be an effect that decreases the epithelial barrier function of the cell layer in the microfluidic system according to the invention. Provided is there for the method of the invention wherein the modulating effect is disrupting or repairing epithelial barrier function. In that respect it is of interest to note that experiments were performed that showed that initially a compound decreased epithelial barrier function (as witnessed by a change of the signal at the acceptor side (in this case in the gel/at the basolateral side)) while at a later time point epithelial barrier function was improved again, even in the presence of said compound. This illustrates that the method of the invention allows for detecting more precisely the modulating effect of a compound on barrier function in comparison to those methods in the art.

Also provided is the method of the invention wherein in step d) the probe is provided to the epithelial cells before the test compound is provided, and preferably wherein after the probe is provided the signal provided by the probe in the microfluidic channel or in the gel, or both in the microfluidic channel and in the gel is determined at various time points and before the test compound is provided.

Such an embodiment is useful to provide data for comparison, as a control, or for determining whether the layer of cells can be used for determining the effect of test compounds on the barrier function. For example, if the measurement without the test compound already reveals there is high transport of the probe, the layer of cells may be rejected for further use in the method of the invention. At the same time, this embodiment allows for determining "background" activity.

With the method of the invention it has now become possible to measure simultaneously/concurrently (that is to say within one and the same experiment) many different test conditions, allowing for methods of screening. The skilled person understands that the word "simultaneously" or "concurrently" is here to denote within the same experiment. The measurements of the signal within the same experiment may be performed sequentially or parallel if so desired.

Therefor the method of the invention may be performed using multiple microfluidic channels comprising epithelial cells at the same time. In a preferred embodiment, the method is a method wherein the microfluidic system comprises at least 3, preferably more than 10, even more preferably about 40, 96, 256, 384 microfluidic channels, preferably wherein at least 3, preferably more than 10, even more preferably about 40, 96, 256, 384 microfluidic channels comprising the epithelial cell layer or tube are measured concurrently, sequentially or in parallel.

The probe used in the method of the invention may be any probe that can be suitable used in determining epithelial barrier function as defined herein. Such probes used in examining diffusion across a layer of epithelial cells are well known to the skilled person. Well-known examples of such probes include Lucifer yellow, fluorescent labeled dextran's or inulin's, for example fluorescein or rhodamine conjugated dextran's or inulin's, FITC-conjugated dextran, TRITC-conjugated dextran and FITC-conjugated inulin at various molecular weights. Typical molecular weight used are 6 kDA, 75 kDA, 150 kDa or 400 kDA for FITC dextran, but other molecular weight may also be used.

In some embodiments, more than one probe is used, and wherein for example each probe is characterized by a different size and/or by a different detectable label. For example different size dextrans or inulins may be used, conjugated to different fluorescent group, for example FITC (Fluorescein isothiocyanate), nanodots, rhodamine (tetramethyl rhodamine isothiocyanate, TRITC) and the like.

Clearly any type of reporter molecule can be used in the context of the method of invention, for example, Fluorescently labeled probes with any fluorophore (e.g., Alexa Fluor® 350, Alexa Fluor® 647, Oregon Green®, Alexa Fluor® 405, Alexa Fluor® 680, Fluorescein (FITC), Alexa Fluor® 488, Alexa Fluor® 750, Cy®3, Alexa Fluor® 532, Pacific Blue™, Pacific Orange™, Alexa Fluor® 546, Coumarin, Tetramethylrhodamine (TRITC), Alexa Fluor® 555, BODIPY® FL, Texas Red®, Alexa Fluor® 568, Pacific Green™, Cy®5, Alexa Fluor® 594, DNA stains, DAPI, SYTOX® Green, SYTO® 9, TO-PRO®-3, Propidium Iodide, Qdot® probes, Qdot® 525, Qdot® 565, Qdot® 605, Qdot®655, Qdot® 705, Qdot® 800, Fluorescent protein labels, R-Phycoerythrin (R-PE), Allophycocyanin (APC) Expressed fluorescent proteins, CFP, GFP (emGFP), RFP (tagRFP)), and so on.

Suitable non-fluorescent luminescent probes include GSH-Glo, MAO-Glo, Pgp-Glo, BacTiter-Glo, Viral Tox, GloNAD, (P)H-Glo, GSH-Glo, and so on.

Colorimetric probes include AEC, AEC+, BCIP/NBT, DAB+, Fuchsin+, Permanent Red, alamar blue, MTT, Griess, and so on.

The skilled person is well aware how to select a suitable probe for use in the method of the invention.

In respect of the above, in a preferred embodiment probes of different size are provided in step d), preferably wherein each different seized probe is labeled with a different fluorescent label.

Also provided is the method of the invention, wherein an overpressure is applied to the side (basolateral or apical) where the probe is provided, preferably wherein the overpressure is realized by adding a higher quantity of fluid to the side where the probe is provided or to the reservoirs corresponding to the side where the probe is provided, compared to the quantity of fluid at the other side, or in the reservoirs corresponding to the other side.

Also provided is the method of the invention wherein the gel is structured in the microfluidic channel by means of capillary pressure techniques, such as pillars, ridges, groves, hydrophobic patches or less hydrophilic patches in a predominantly more hydrophilic channel.

Also provided is a method of the invention, preferably the method of claim 19 as filed, wherein one or more probes are provided to the epithelial cells together with or at time points after addition of the test compound, and a first probe, and wherein the one or more probes are distinguishable from the first probe, preferably by optical means.

Having now generally described the invention, the same will be more readily understood through reference to the following examples which is provided by way of illustration and is not intended to be limiting of the present invention.

EXAMPLES

FIG. 1 shows seeding of a barrier against an ExtraCellular Matrix in the microfluidic platform:
A) Schematic of seeding cells against an ExtraCellular Matrix (ECM). In the 2-lane microfluidic platform an ECM is seeded in a gel channel. After hardening of the ECM cells are seeded in culture medium in the culture channel. The plate is incubated on its side to allow the cells to settle on top of the ECM by gravity. After attachment of the cells the perfusion flow is initiated. Cell-type dependent, a cellular barrier is formed against the ECM or coating the entire medium perfusion channel forming a tubular structure. B) Example of the formation of a tubular structure in the medium perfusion channel. The pig proximal tubule cells LLC-PK1 are seeded in the medium perfusion channel against an ECM. 1 day after seeding a layer of cells is observed by phase contrast microscopy lying against the ECM. On day 4 cells are growing against all four sides of the medium perfusion channel. On day 6 a confluent monolayer is formed all around.

Figure 2:
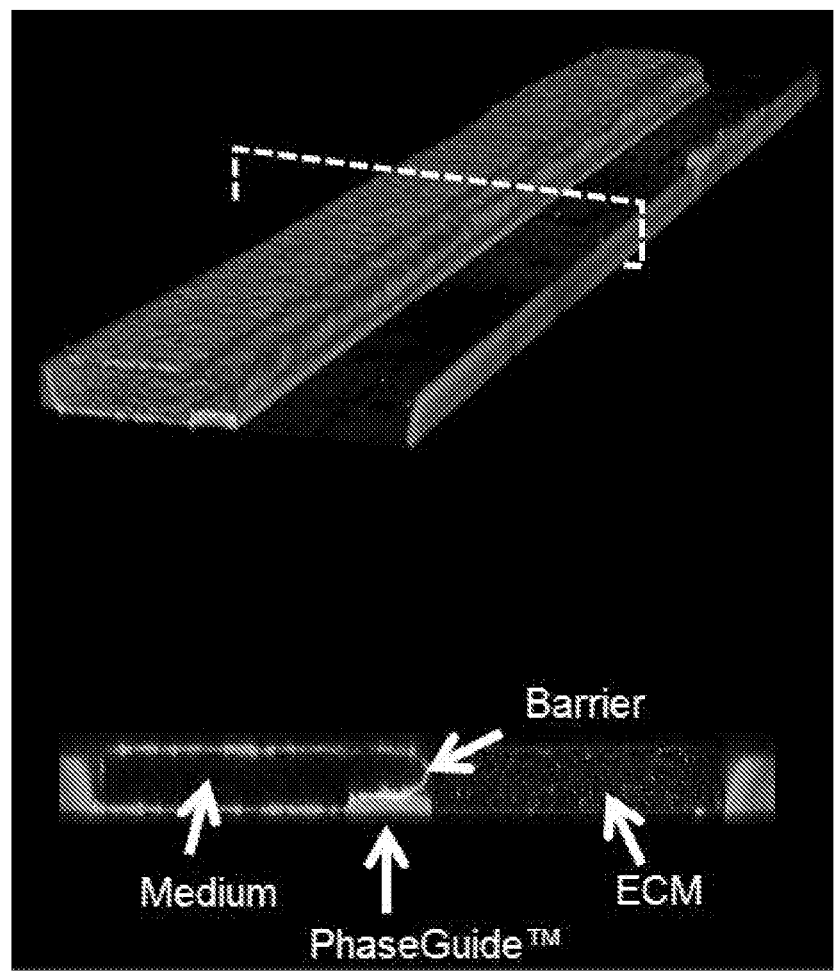
FIG. 2 shows a 3D confocal image of a barrier in a 2-lane microfluidic chip: The canine proximal tubule cells MDCK were seeded against an ECM in a 2-lane microfluidic device as described in FIG. 1.

FIG. 2 shows a 3D confocal image of a barrier in a 2-lane microfluidic chip:
The canine proximal tubule cells MDCK were seeded against an ECM in a 2-lane microfluidic device as described in FIG. 1. After barrier formation was observed by phase contrast microscopy the cells were stained with the viability dye calcein-AM (Life Technologies, C1430), labelling the viable cells fluorescently green. After fixation cells were stained with ActinRed (Life Technologies, R37112) and imaged by confocal microscopy (Leica, TCS SP5 STED). 3D projection was created using the 3D viewer Fiji plug in (Schindelin, J.; Arganda-Carreras, I. & Frise, E. et al. (2012), "Fiji: an open-source platform for biological-image analysis", Nature methods 9(7): 676-682, PMID 22743772). The slice shows the formation of a confluent barrier of cells against the ECM. The apical side of the barrier can be accessed through the medium perfusion channel, while the basal side has free access from the gel channel.

Figure 3A:
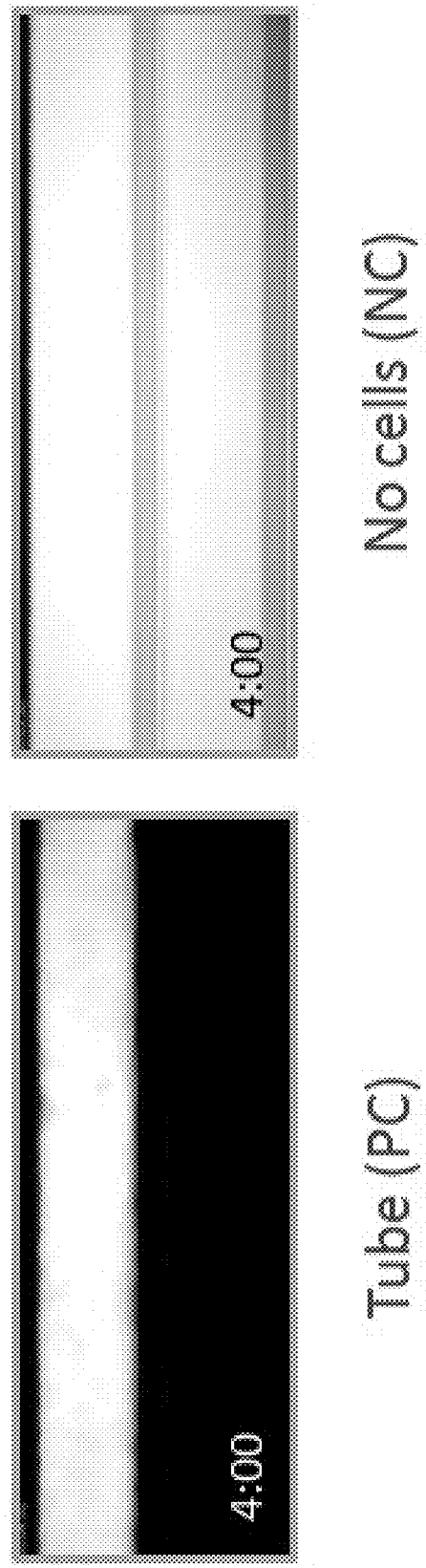
FIG. 3A-3C: Barrier Integrity Assay: The integrity of a cellular barrier, cultivated for example as described in FIG. 1 and FIG. 2, can be probed by replacing the medium in the perfusion channel by medium containing 500 μg/mL FITC-dextran 150 kDa (Sigma, 46946). A) If the cellular barrier is leak-tight the fluorescent signal will be contained in the perfusion channel, whereas in the microfluidic chip with no cells, just ECM in the gel channel, the fluorescent signal will enter the ECM and will saturate within minutes. B) Fluorescent signal intensity of the FITC-dextran 150 kDa was quantified in the top perfusion channel and in the gel channel using FIJI analysis software (Schindelin, J.; Arganda-Carreras, I. & Frise, E. et al. (2012), "Fiji: an open-source platform for biological-image analysis", Nature methods 9(7): 676-682, PMID 22743772.). C) The intensity of the gel channel was divided by the intensity of the top perfusion channel and the ratio was plotted against the time after start of fluorescent reporter addition.
Figure 3B:
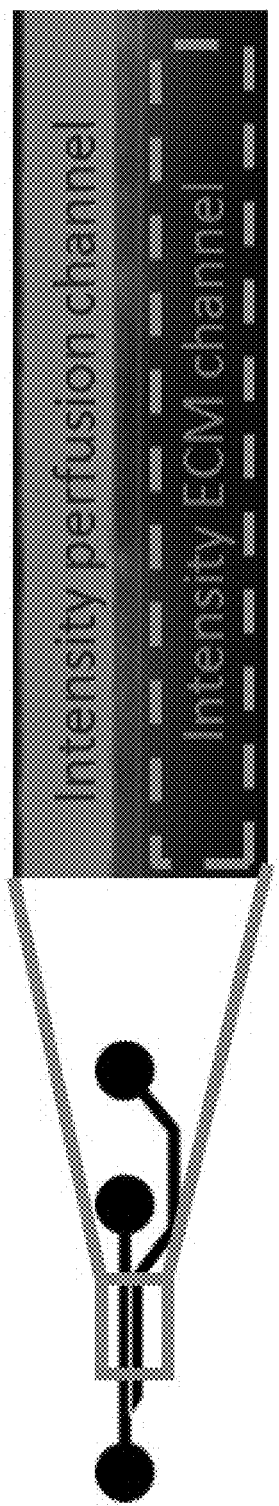
Figure 3C:
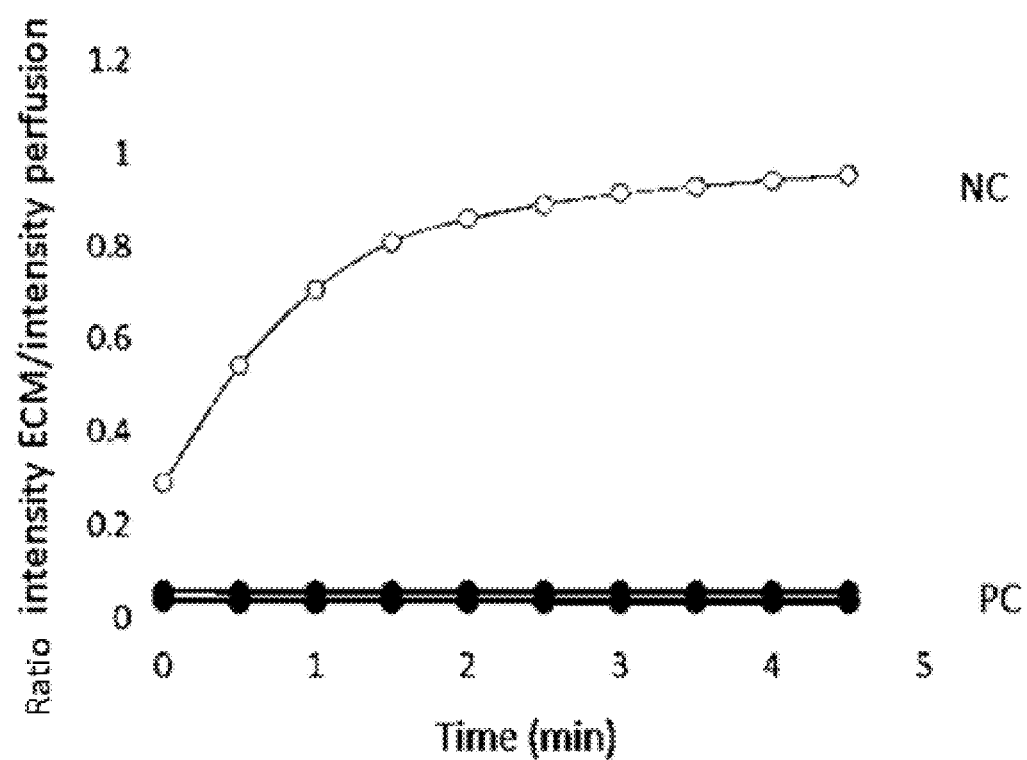

FIG. 3: Barrier Integrity Assay:
The integrity of a cellular barrier, cultivated for example as described in FIGS. 1 and 2, can be probed by replacing the medium in the perfusion channel by medium containing 500 µg/mL FITC-dextran 150 kDa (Sigma, 46946). A) If the cellular barrier is leak-tight the fluorescent signal will be contained in the perfusion channel, whereas in the microfluidic chip with no cells, just ECM in the gel channel, the fluorescent signal will enter the ECM and will saturate within minutes. The fluorescent signal in the perfusion and gel channel can be monitored real time using time-lapse fluorescent microscopy, as for example with the ImageXpress Micro (Molecular Devices). B)
Fluorescent signal intensity of the FITC-dextran 150 kDa was quantified in the top perfusion channel and in the gel channel using FIJI analysis software (Schindelin, J.; Arganda-Carreras, I. & Frise, E. et al. (2012), "Fiji: an open-source platform for biological-image analysis", Nature methods 9(7): 676-682, PMID 22743772). C) The intensity of the gel channel was divided by the intensity of the top perfusion channel and the ratio was plotted against the time after start of fluorescent reporter addition. Without a cellular barrier the ECM is saturated within minutes after dye addition whereas a ratio close to zero is maintained as long as the cellular barrier is intact.

Figure 4:
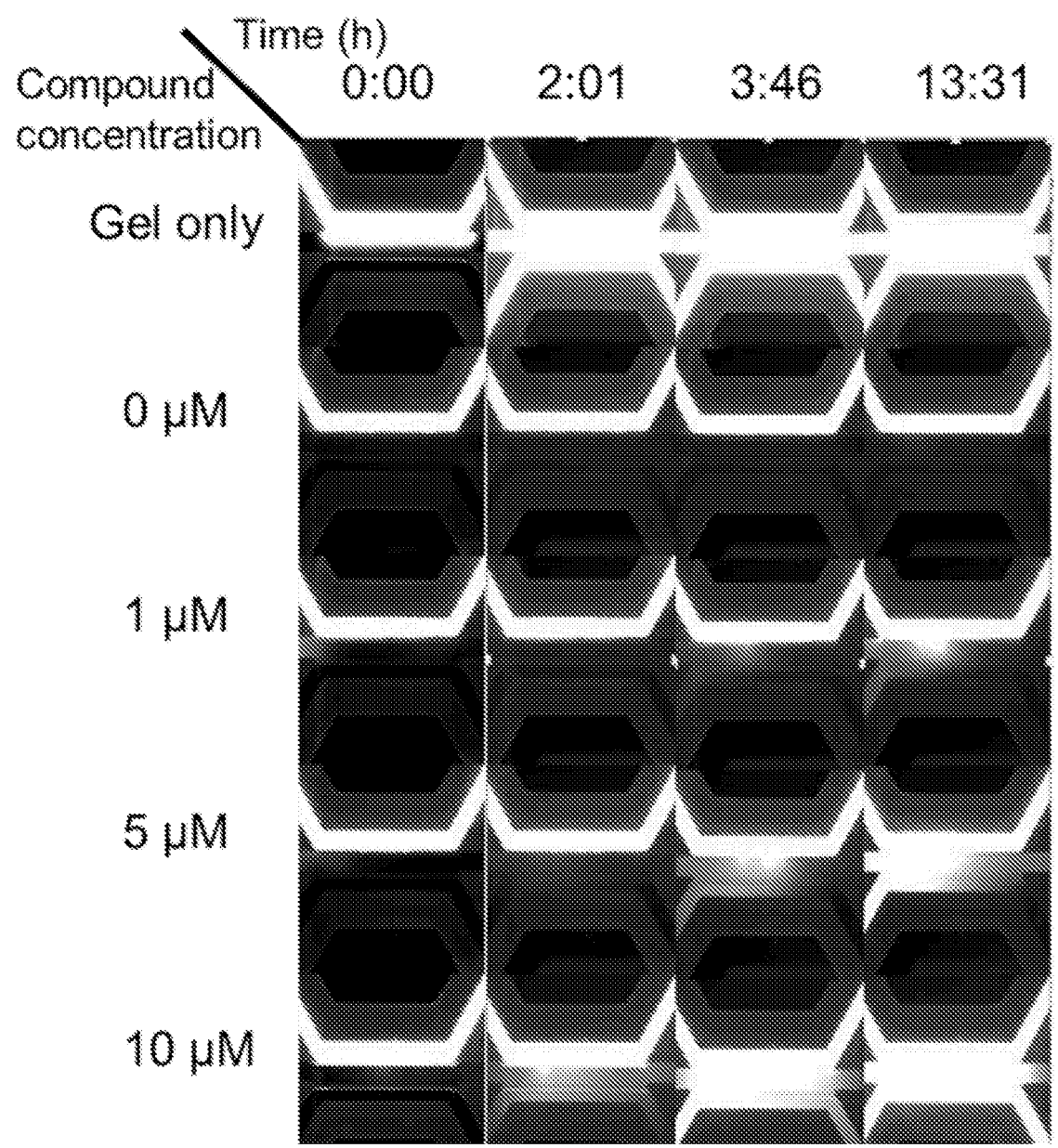
FIG. 4 shows barrier Integrity Assay LLC-PK1 with staurosporin exposure.

FIG. 4 shows barrier Integrity Assay LLC-PK1 with staurosporin exposure:
The pig proximal tubule cell line LLC-PK1 (ATCC, CL-101, passage 210) was seeded at 10*106 cells/mL in the top perfusion channel of a 200 µm 3-lane OrganoPlate™ against a collagen I ECM (Cultrex, Amsbio, 3447-020-01, 4 mg/mL). 60 µL of medium was added to the medium inlet and outlet of the top perfusion channel. Plate was incubated on its side overnight to allow cells to settle on top of the ECM. On day 1 after seeding 60 µL medium was added to the medium inlet and outlet of the bottom perfusion channel and plate was placed flat in the incubator. On day 4 after seeding plate was placed on a rocker platform for continuous medium perfusion (angle 7°, tilt every 8 min). On day 6 after seeding leak-tightness of the LLC-PK1 tubules was tested by replacing the medium in the top perfusion channel by medium containing 500 µg/mL FITC-dextran 150 kDa (Sigma, 46946). Volumes were 60 µL/40 µL in top perfusion channel, 0 µL/0 µL in the middle ECM channel, 40 µL/40 µL standard culture medium in the bottom perfusion channel. Tubules that did not show FITC-dextran signal in the ECM 15 min after addition were considered leak-tight and selected for staurosporin exposure. Medium in the top perfusion channel was replaced by medium containing 500

μg/mL FITC-dextran 150 kDa and 0, 1, 5 or 10 μM of the pan-kinase inhibitor staurosporin (Sigma, S4400). Volumes were 60 μL/40 μL in top perfusion channel, 0 μL/0 μL in the middle ECM channel, 40 μL/40 μL standard culture medium in the bottom perfusion channel. Plate was placed on an EVOS FL auto (Live Technologies) under 5% CO2, 37° C., humidified incubation conditions. Microfluidic chips were phase contrast and fluorescently (FITC) imaged with a 4× objective, every 15 min for 16 hours. Representative time points are shown. With no exposure to staurosporin the LLC-PK1 tube remains leak-tight over the length of the experiment. With increasing concentrations of staurosporin the integrity of the LLC-PK1 barrier breaks at an earlier time point.

Figure 5:
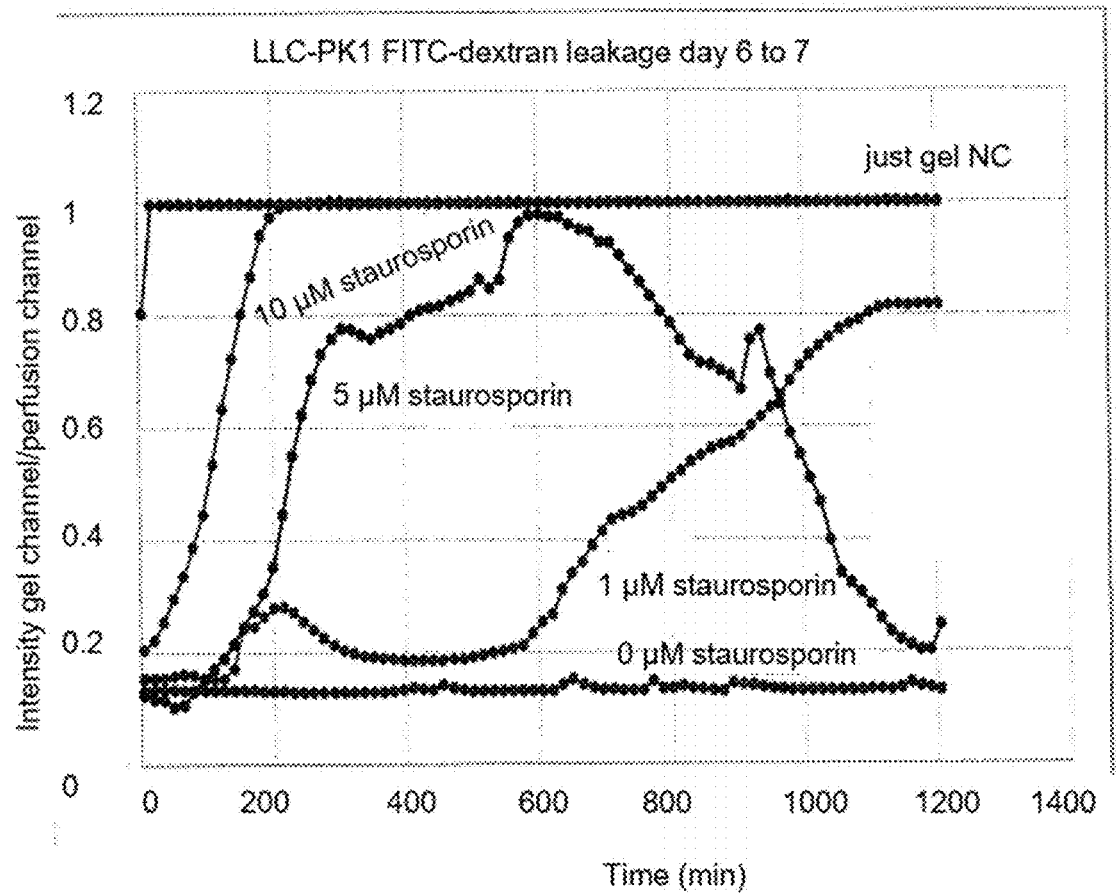
FIG. 5 shows quantification of the barrier Integrity Assay LLC-PK1 with staurosporin exposure.

FIG. 5 shows quantification of the barrier Integrity Assay LLC-PK1 with staurosporin exposure: Fluorescent signal intensity of the FITC-dextran 150 kDa was quantified in the top perfusion channel and in the gel channel of FIG. 4 using FIJI analysis software (Schindelin, J.; Arganda-Carreras, I. & Frise, E. et al. (2012), "Fiji: an open-source platform for biological-image analysis", Nature methods 9(7): 676-682, PMID 22743772). The intensity of the gel channel was divided by the intensity of the top perfusion channel and the ratio was plotted against the time after start of staurosporin exposure. An increase in ratio means an increase in the fluorescent signal in the gel channel implying a breach in the LLC-PK1 barrier integrity.

Figure 6:
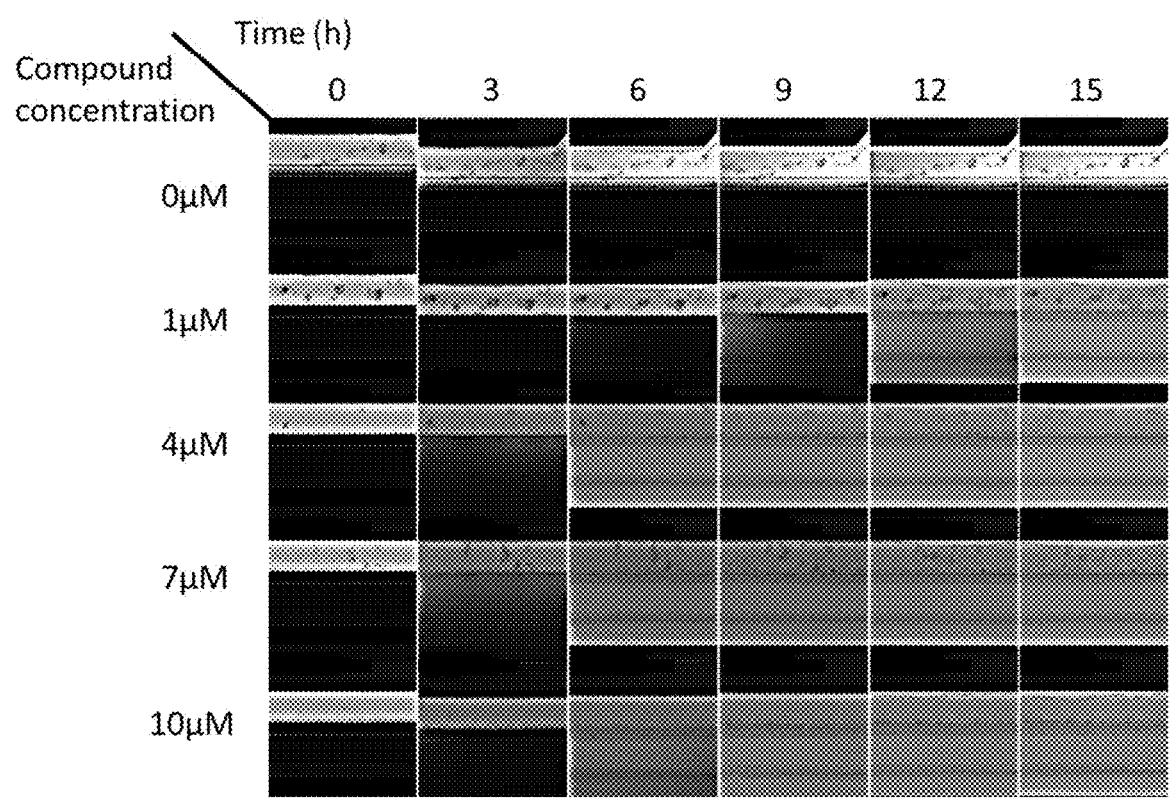
FIG. 6 shows a similar experiment as described in FIG. 4, with a kidney tubule cell line of different origin.

FIG. 6 shows a similar experiment as described in FIG. 4, with a kidney tubule cell line of different origin. MDCK (canine) cell line was seeded at $10*10^6$ cells/mL in the top perfusion channel of a 400 μm 3-lane OrganoPlate® against a collagen I ECM (Cultrex, Amsbio, 3447-020-01, 4 mg/mL). 60 μL of medium was added to the medium inlet and outlet of the top perfusion channel. Plate was incubated on its side for 3 hours to allow cells to settle on top of the ECM. Three hours after seeding 60 μL medium was added to the medium inlet and outlet of the bottom perfusion channel and plate was placed on a rocker platform for continuous medium perfusion (angle 7°, tilt every 8 min). On day 5 after seeding leak-tightness of the MDCK tubules was tested by replacing the medium in the top perfusion channel by medium containing 500 μg/mL FITC-dextran 150 kDa (Sigma, 46946). Volumes were 40 μL inlet/30 μL outlet in top perfusion channel, 0 μL inlet/0 μL outlet in the middle ECM channel, 20 μL inlet/20 μL outlet standard culture medium in the bottom perfusion channel. Tubules that did not show FITC-dextran signal in the ECM 15 min after addition were considered leak-tight and selected for staurosporin exposure. Medium in the top perfusion channel was replaced by medium containing 500 μg/mL FITC-dextran 150 kDa and 0, 1, 4, 7 or 10 μM of the pan-kinase inhibitor staurosporin (Sigma, S4400). Volumes were 40 μL inlet/30 μL outlet in top perfusion channel, 0 μL inlet/0 μL outlet in the middle ECM channel, 20 μL inlet/20 μL outlet standard culture medium in the bottom perfusion channel. Plate was placed on the high content screen ImageXpress Micro XLS (Molecular Devices) under 5% CO2, 37° C., and humidified incubation conditions. Microfluidic chips were fluorescently (FITC) imaged with a 4× objective, every hour for 15 hours. Representative time points are shown. With no exposure to staurosporin the MDCK tube remains leak-tight over the length of the experiment. With increasing concentrations of staurosporin the integrity of the MDCK barrier breaks at an earlier time point.

Figure 7:
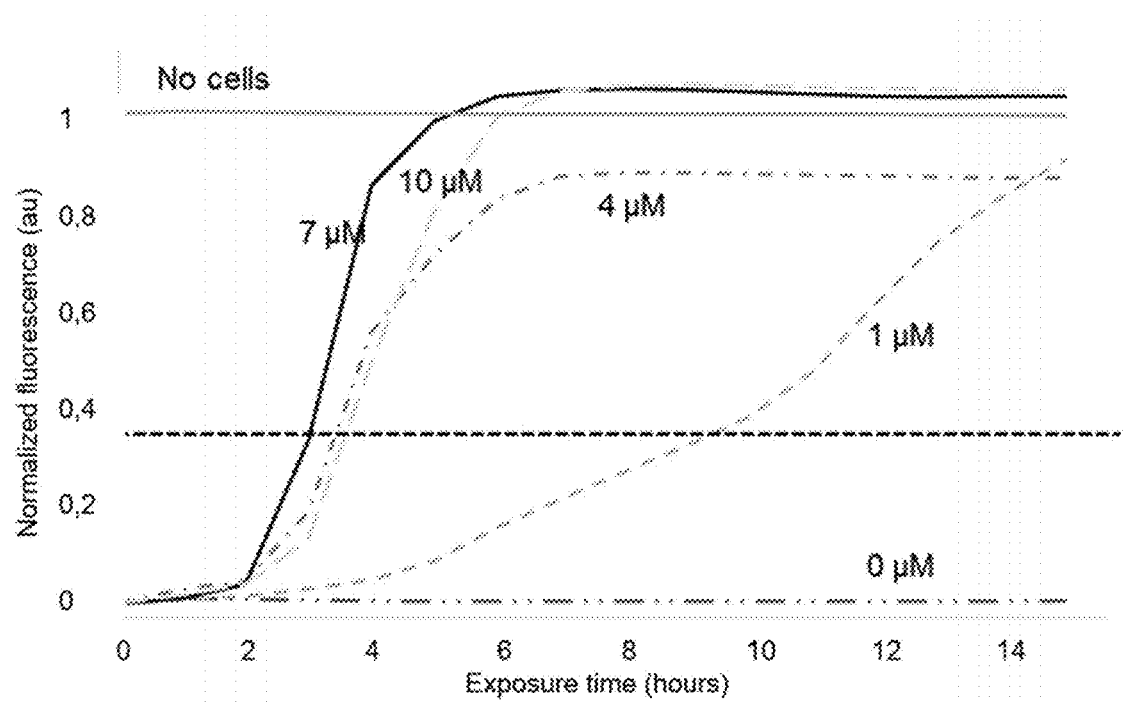
FIG. 7 shows quantification of the barrier Integrity Assay with MDCK with staurosporin exposure from FIG. 6.

FIG. 7 shows quantification of the barrier Integrity Assay with MDCK with staurosporin exposure from FIG. 6. Fluorescent signal intensity of the FITC-dextran 150 kDa was quantified in the top perfusion channel and in the gel channel of FIG. 4 using FIJI analysis software (Schindelin, J.; Arganda-Carreras, I. & Frise, E. et al. (2012), "Fiji: an open-source platform for biological-image analysis", Nature methods 9(7): 676-682, PMID 22743772). The intensity of the gel channel was divided by the intensity of the top perfusion channel and the ratio was plotted against the time after start of staurosporin exposure. An increase in ratio means an increase in the fluorescent signal in the gel channel implying a breach in the MDCK barrier integrity. Time-to-leakage concentration determination: A threshold can be set for the intensity ratio, e.g. 0.4. The time point corresponding to this ratio for each exposed compound concentration is plotted against the concentration. A compound characteristic concentration based on the time-to-leakage, comparable to the IC50 value, can be determined. The time-to-leakage value (e.g. 2 hours after compound addition) will have to be determined based on validation experiments to ensure maximal in vivo relevance. This time-to-leakage time point can be set at the same value for all compounds (as it is for the IC50 value), or could be made dependent e.g. the half-life of a compound.

Figure 8:
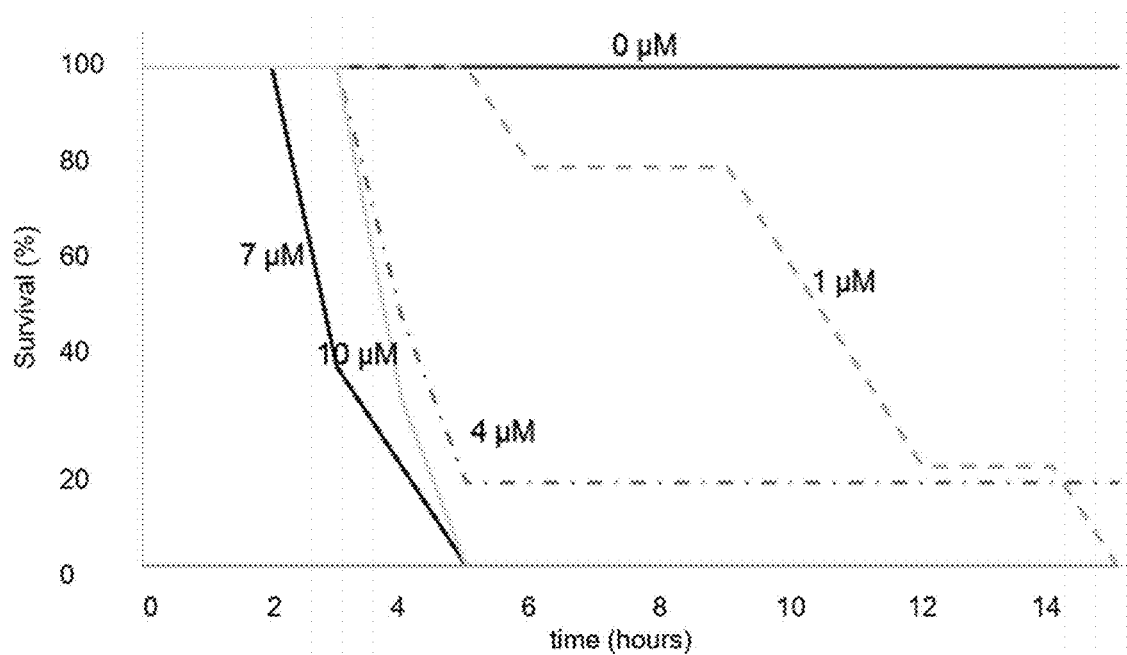
FIG. 8 shows further data interpretation of the graph in FIG. 7.

FIG. 8 shows further data interpretation of the graph in FIG. 7. At the time point a tube passes the fluorescent threshold ratio (here set at 0.4) a tube is considered breached. Loss of barrier integrity can be plotted in a so called survival plot (Kaplan Meier plot) as depicted here. This approach is particularly useful when insufficient data points are available for accurate EC50 determination. An example thereof is given in FIG. 11.

Figure 9:
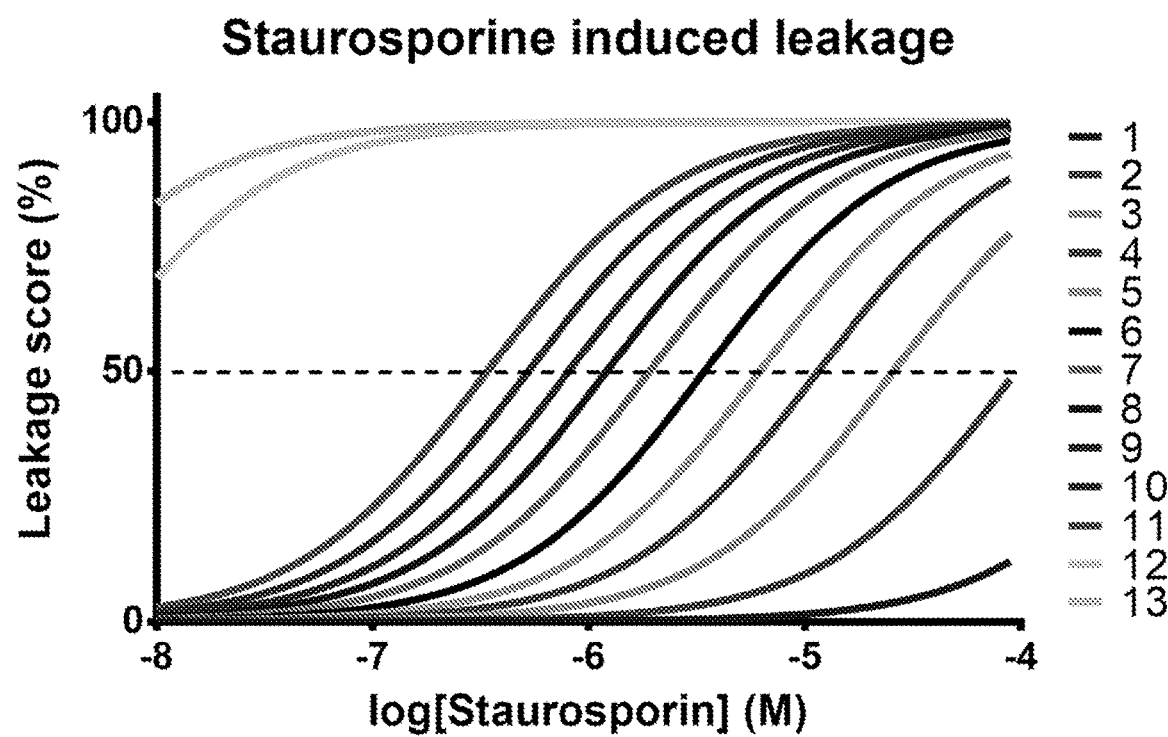
FIG. 9 shows the dose response curve extracted at every time for a time-to-leak barrier integrity assay on a human gut tubule exposed to staurosporin.

FIG. 9 shows the dose response curve extracted at every time for a time-to-leak barrier integrity assay on a human gut tubule exposed to staurosporin. The Caco-2 cell line (Sigma, human colon carcinoma cells) was seeded in a 400 μm 3 lane OrganoPlate® at 10E6 cells/mL, placed on side for cell-ECM attachment for 2 hours, and then placed on a modified rocker platform for continuous medium perfusion. Three days after seeding leak-tightness of the Caco-2 tubules was tested by replacing the medium in the top perfusion channel with medium containing 0.25 mg/mL TRITC dextran 150 kDa. Tubules that showed no fluorescent dye leakage into the ECM compartment for 30 min were considered leak-tight and used for the compound exposure. Medium in the top medium channel was replaced with medium with TRITC-dextran and increasing concentrations of aspirin. Plate was placed in the ImageXpress Micro XLS under temperature and CO2 controlled conditions and imaged for fluorescent (TRITC) signal every hour for 13 hours. A dose response curve can be extracted at every time point from the time-lapse of the exposed Caco-2 tubes. GraphPad Prism 6 (GraphPad Software Inc., La Jolla, Calif.) was used to fit the dose response curve based on nonlinear regression of the logarithm of the compound concentration versus the normalized fluorescence assuming a top and bottom plateau at 0 and 100% fluorescence. With increasing exposure times, a shift towards lower compound concentrations is observed.

Figure 10:
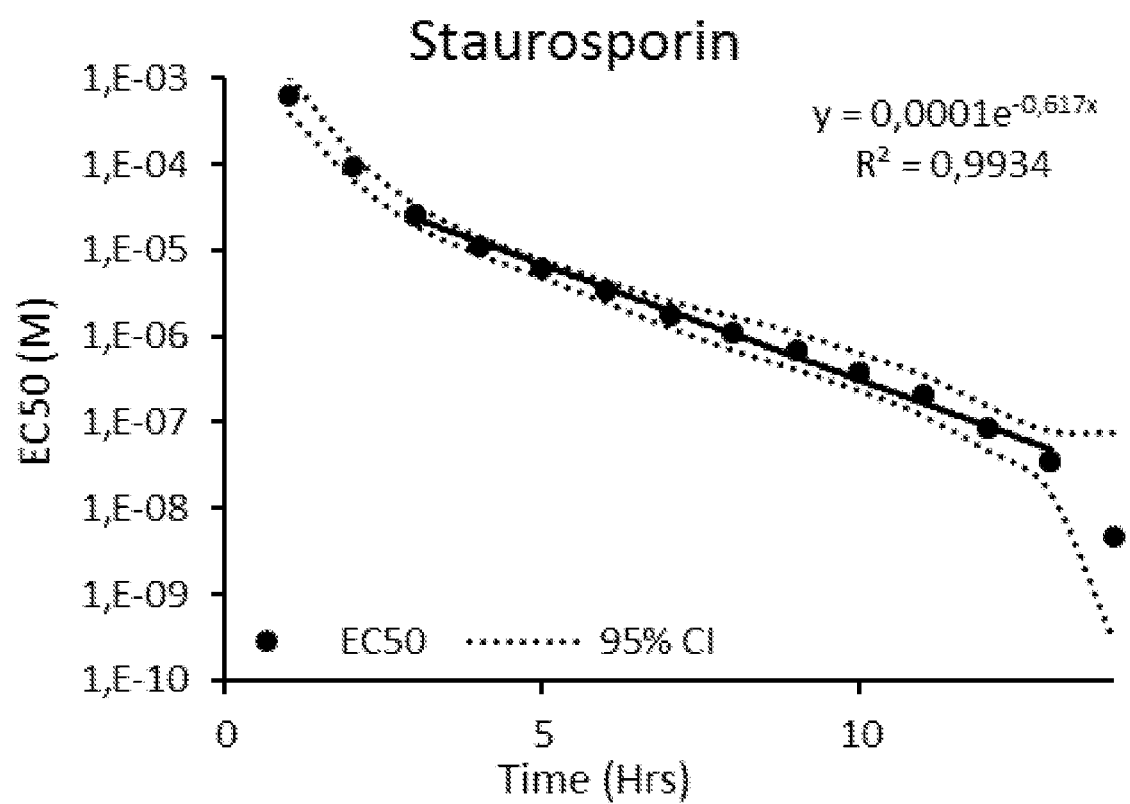
FIG. 10 shows the exponential decrease of the EC50 value of the dose response of the Caco-2 tube from FIG. 9 over time.

FIG. 10 shows the exponential decrease of the EC50 value of the dose response of the Caco-2 tube from FIG. 9 over time. This is observed when plotting the extracted EC50 values against time. The 95% confidence interval of the extracted EC50 values indicates robust data between 3 and 13 hours of exposure.

Figure 11:
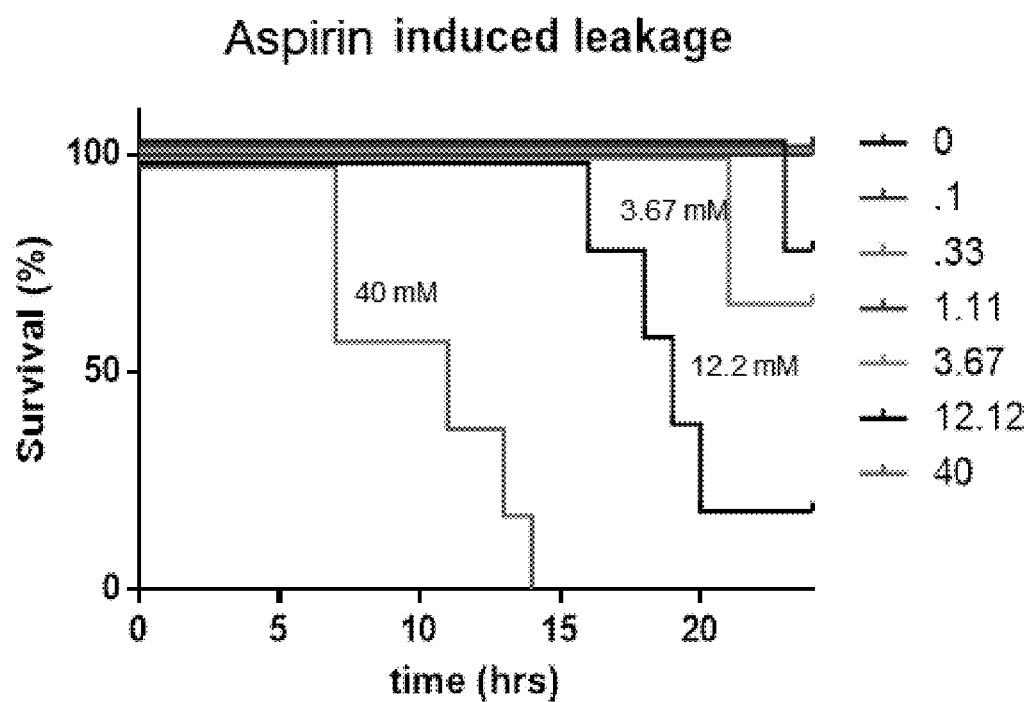
FIG. 11 depicts the loss of barrier function of a gut tubule exposed to aspirin.

FIG. 11 depicts the loss of barrier function of a gut tubule exposed to aspirin. The Caco-2 cell line (Sigma, human colon carcinoma cells) was seeded in a 400 μm 3 lane OrganoPlate® at 10E6 cells/mL, placed on side for cell-ECM attachment for 2 hours, and then placed on a modified rocker platform for continuous medium perfusion. Three days after seeding leak-tightness of the Caco-2 tubules was tested by replacing the medium in the top perfusion channel with medium containing 0.25 mg/mL TRITC dextran 150 kDa. Tubules that showed no fluorescent dye leakage into the ECM compartment for 30 min were considered leak-tight and used for the compound exposure. Medium in the top medium channel was replaced with medium with TRITC-dextran and increasing concentrations of aspirin. Plate was placed in the ImageXpress Micro XLS under temperature and CO2 controlled conditions and imaged for fluorescent (TRITC) signal every hour for 24 hours. Although aspirin is a less potent toxicant to the gut, fluorescence data show loss of barrier function at 40 mM and 12.12 mM concentrations. However, the lack of data on concentrations with a maximum response hinders accurate EC50 estimation. The Kaplan-Meier curve depicted here however shows a highly significant trend of loss of barrier function at higher concentration (P<0.0001 for both curve difference and trend significance). In the OrganoPlate®-based assay we observed clear loss of barrier integrity at both 40 and 12 mM concentrations and even at 3.7 mM. Although no true dose response curve can be accurately fitted, a 50% effect was observed for 40 mM at 10 hours of exposure, and 12 mM at 20 hours of exposure.

Figure 12:
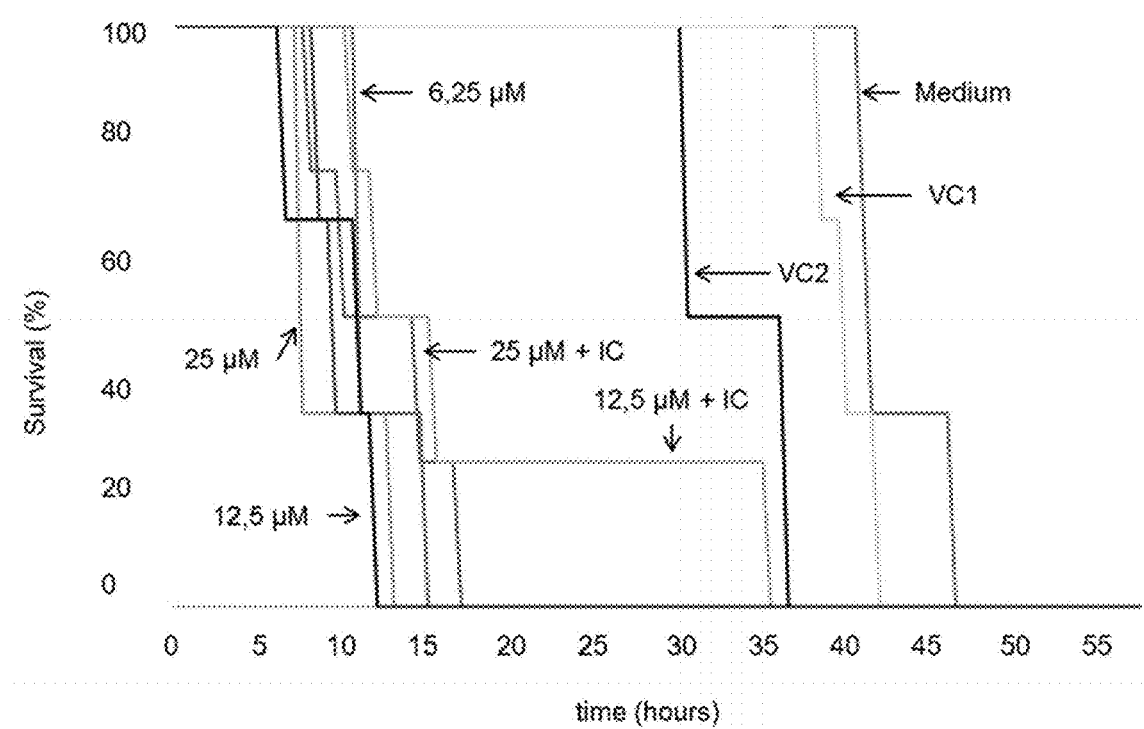
FIG. 12 shows the Kaplan-Meier plot for the drug induced loss of barrier integrity of a human kidney proximal tubule exposed to amphotecerin B.

FIG. 12 shows the Kaplan-Meier plot for the drug induced loss of barrier integrity of a human kidney proximal tubule exposed to amphotecerin B. The human proximal tubule cells (RPTEC, Sigma) were seeded in a 400 µm 3 lane OrganoPlate® at 20E6 cells/mL, placed on side for cell-ECM attachment overnight, and then placed on a modified rocker platform for continuous medium perfusion. After eight days in culture >95% of the seeded tubules were shown leak-tight by addition of FITC-dextran 150 kDa to the medium in the luminal compartment. Medium in the tubes was replaced with medium containing increasing concentrations of the renal toxicant amphotecerin B and the fluorescent FITC-dextran. Plate was placed in the ImageXpress Micro XLS under temperature and CO2 controlled conditions and imaged for fluorescent (FITC) signal every hour for 60 hours. The survival of tube integrity depicted here shows a significant difference between the unexposed (medium, vehicle control 1 and vehicle control 2) and the exposed tubes. IC indicates an inhibitor cocktail of 3 efflux transporter inhibitors.

Figure 13:
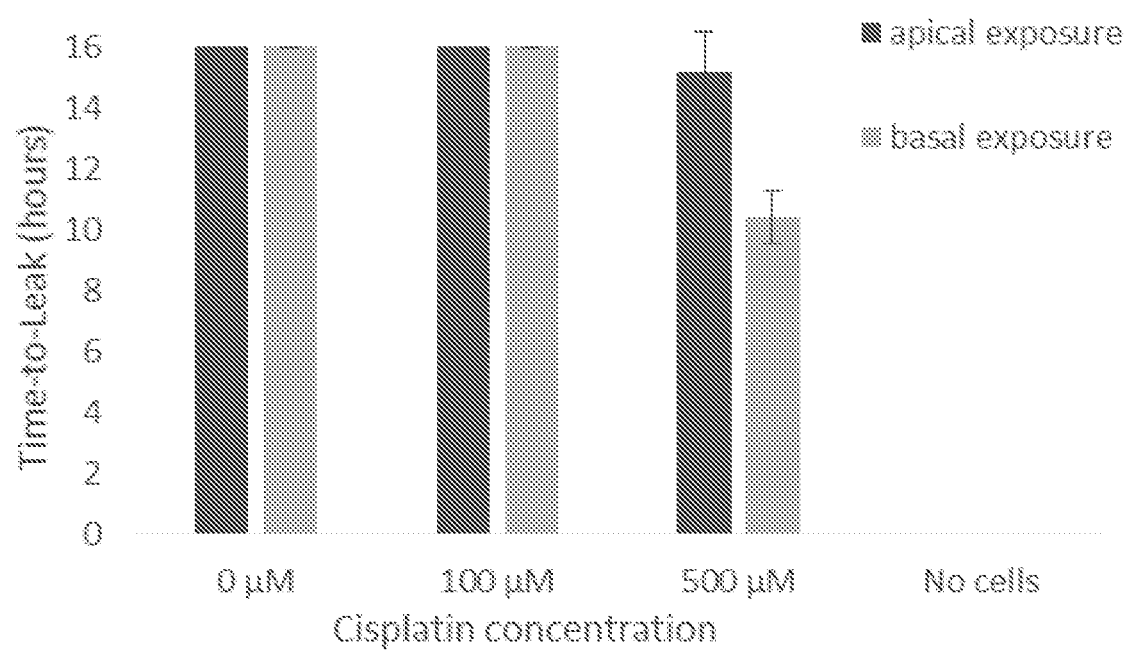
FIG. 13 shows the difference in time-to-leak when a tubule is exposed to a toxic compound only from the apical (luminal) or basolateral side.

FIG. 13 shows the difference in time-to-leak when a tubule is exposed to a toxic compound only from the apical (luminal) or basolateral side. The 3 lane OrganoPlate® offers the unique possibility to add a compound from only the apical or the basolateral side of the tubular structure. Compounds that can passively enter cells through diffusion (e.g. staurosporin) have no directionality in cellular uptake. Actively transported compounds can have directionality in the trans-cellular transport, as is for example the situation in the renal proximal tubules, where moving compounds specifically from the apical side of the tube to the basolateral side, or the other way around, is part of the renal filtering function. This implies toxic compounds that are actively transported by the proximal tubule cells can have a different effect depending on the location of exposure. The anti-cancer drug cisplatin is taken up by cells by the OCT-2 transporter that is expressed on the basal side of the epithelial monolayer. MDCK cells were seeded in the top channel of a 200 µm 3 lane OrganoPlate® against a collagen I ECM at 10E6 cells/mL. Three days after seeding MDCK tubules were exposed to increasing concentrations of cisplatin from either the apical or basal side by replacing the medium either in the top medium channel, or in the bottom medium channel, with medium with cisplatin. At the start of the exposure the medium in the top channel was also supplied with a fluorescent leakage marker, FITC-dextran 150 kDa. Plate was placed in the ImageXpress Micro XLS under temperature and CO2 controlled conditions and imaged for fluorescent (FITC) signal 30 min for 16 hours. The time-to-leak for the tubes exposed from the basal side is significantly earlier than for the apical exposed tubes.

Figure 14A:
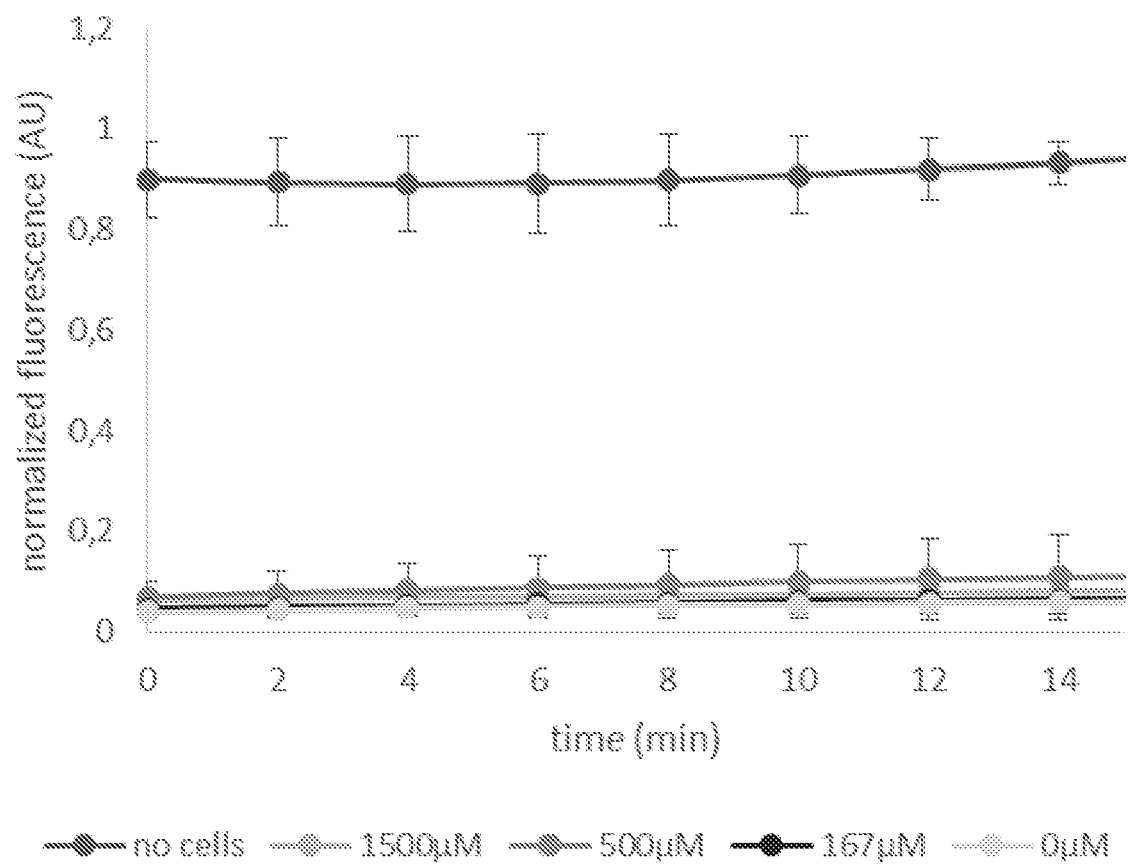
FIG. 14A-14B shows the barrier integrity of renal proximal tubules exposed for 6 days to increasing concentrations of tenofovir. After exposure and the fluorescent read out of the tube integrity the medium in the tubes was replaced with medium with fresh toxic compound and the integrity of the same tubes as in FIG. 14a, and previously unexposed tubes, was determined after 72 hours exposure shown in FIG. 14b.
Figure 14B:
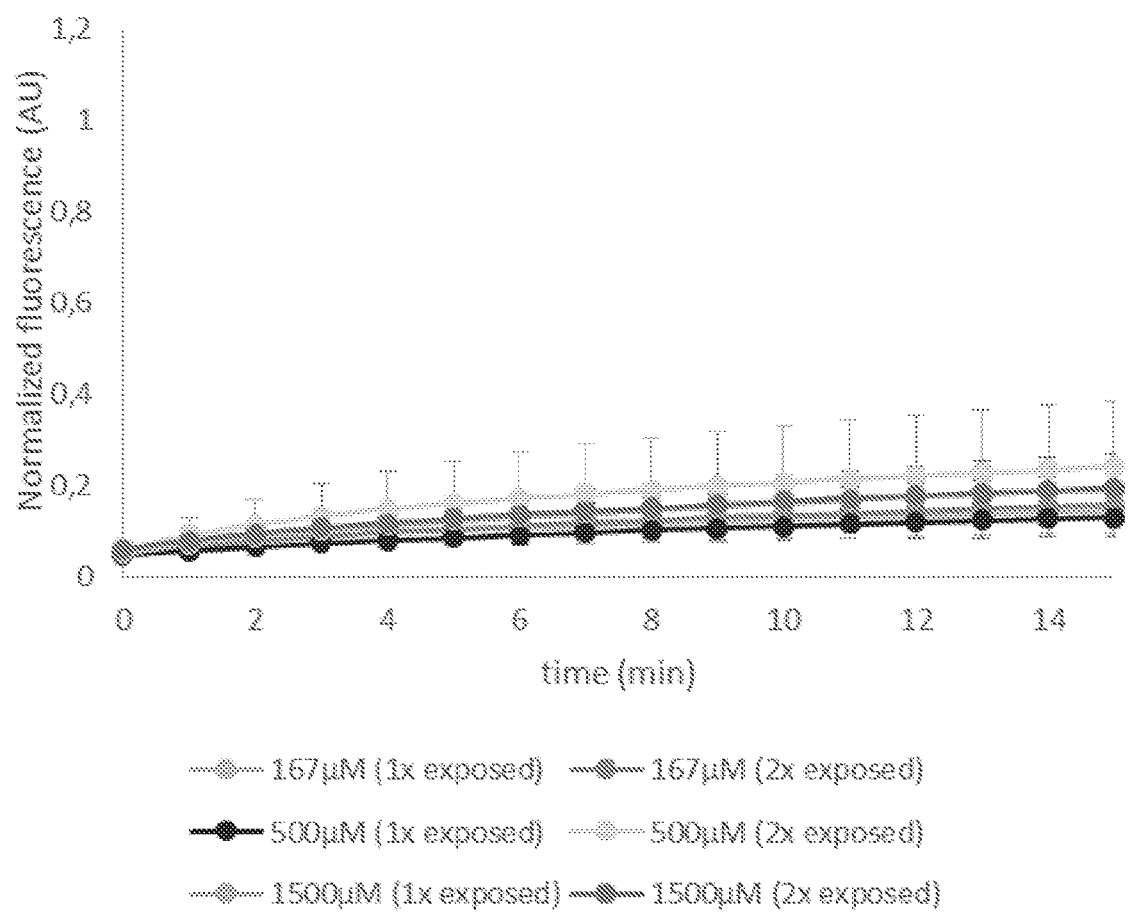

FIG. 14a shows the barrier integrity of renal proximal tubules exposed for 6 days to increasing concentrations of tenofovir. After exposure and the fluorescent read out of the tube integrity the medium in the tubes was replaced with medium with fresh toxic compound and the integrity of the same tubes as in FIG. 14a, and previously unexposed tubes, was determined after 72 hours exposure shown in FIG. 14b.

Figure 15:
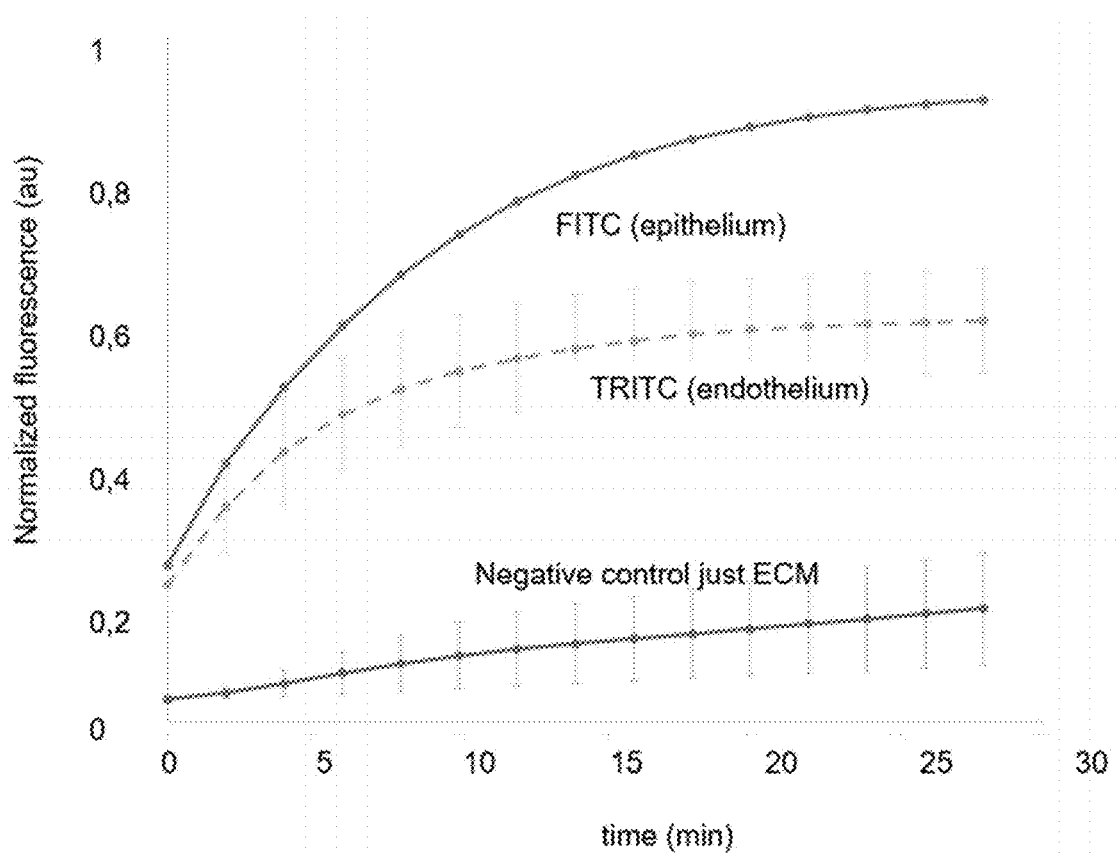
FIG. 15 describes a co-culture of two tubular structures in one 3lane OrganoPlate® with a renal proximal tubule cultured in the top medium channel, which 9 days after seeding was probed with a fluorescent FITC-dextran 150 kDa by replacing the medium in the lumen of the tube.

FIG. 15 describes a co-culture of two tubular structures in one 3 lane OrganoPlate® with a renal proximal tubule cultured in the top medium channel, which 9 days after seeding was probed with a fluorescent FITC-dextran 150 kDa by replacing the medium in the lumen of the tube. The tube in the bottom channel is comprised of endothelial cells (HUVEC), of which the integrity at day 9 is probed with TRITC-dextran 150 kDa. The leakage of the fluorescent probes into the ECM in the middle channel is plotted in FIG. 15.

Figure 16:
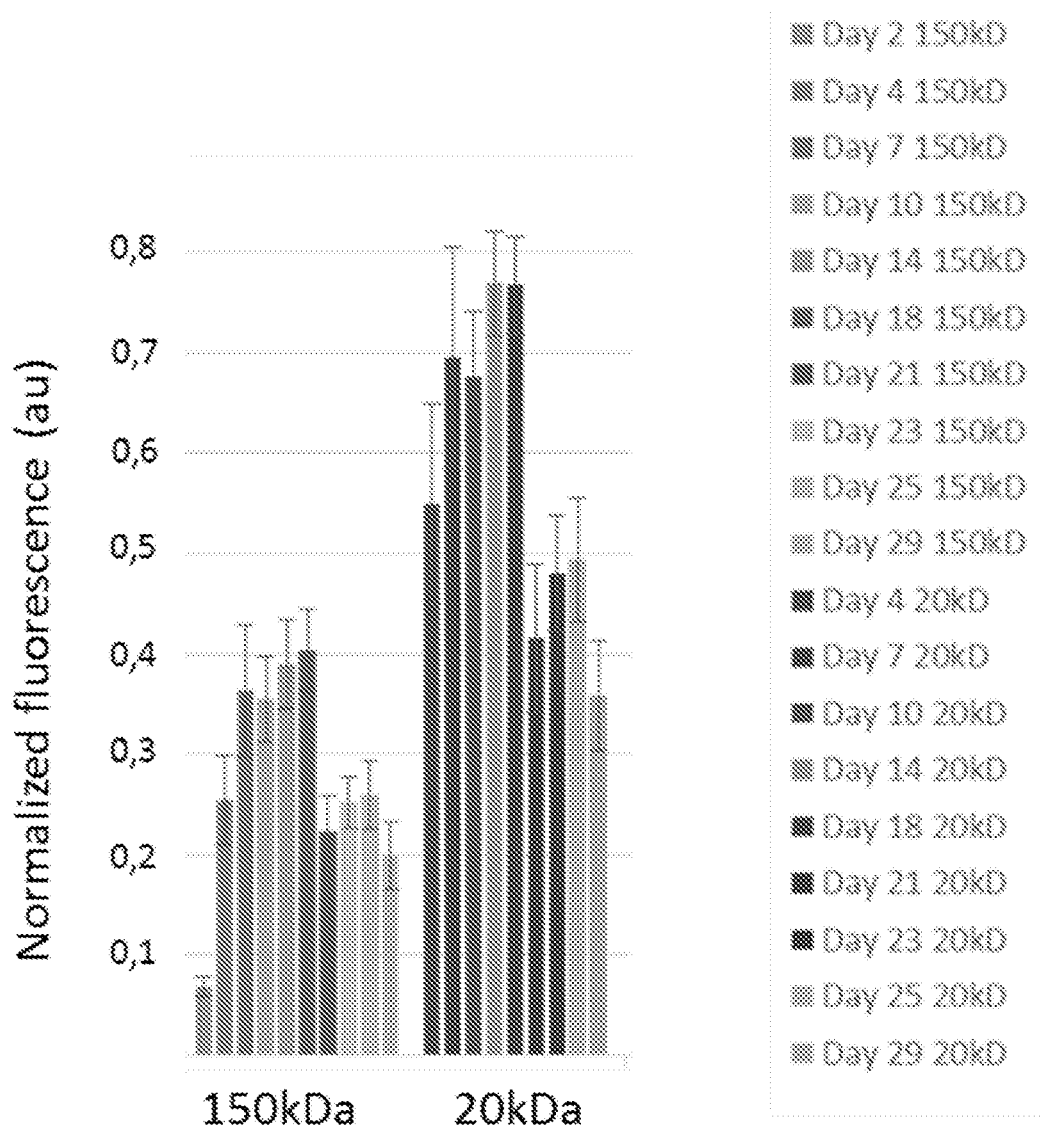
FIG. 16 shows the leak-tightness of endothelial tubes cultured in a 400 μm 2lane OrganoPlate® against a collagen I ECM at different days after seeding showing a leak-tight profile of the same tubules for over 25 days.

FIG. 16 shows the leak-tightness of endothelial tubes cultured in a 400 µm 2 lane OrganoPlate® against a collagen I ECM at different days after seeding showing a leak-tight profile of the same tubes for over 25 days. Leak-tightness is probed by fluorescently labelled dextrans of two different sizes (FITC-dextran 150 kDa and TRITC-dextran 20 kDa) showing a difference in barrier function for differently sized compounds.

Having now fully described this invention, it will be appreciated by those skilled in the art that the same can be performed within a wide range of equivalent parameters, concentrations, and conditions without departing from the spirit and scope of the invention and without undue experimentation.

While this invention has been described in connection with specific embodiments thereof, it will be understood that it is capable of further modifications. This application is intended to cover any variations, uses, or adaptations of the inventions following, in general, the principles of the invention and including such departures from the present disclosure as come within known or customary practice within the art to which the invention pertains and as may be applied to the essential features hereinbefore set forth as follows in the scope of the appended claims.

All references cited herein, including journal articles or abstracts, published or corresponding patent applications, patents, or any other references, are entirely incorporated by reference herein, including all data, tables, figures, and text presented in the cited references. Additionally, the entire contents of the references cited within the references cited herein are also entirely incorporated by references.

Reference to known method steps, conventional methods steps, known methods or conventional methods is not in any way an admission that any aspect, description or embodiment of the present invention is disclosed, taught or suggested in the relevant art.

The foregoing description of the specific embodiments will so fully reveal the general nature of the invention that others can, by applying knowledge within the skill of the art (including the contents of the references cited herein), readily modify and/or adapt for various applications such specific embodiments, without undue experimentation, without departing from the general concept of the present invention. Therefore, such adaptations and modifications are intended to be within the meaning and range of equivalents of the disclosed embodiments, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance presented herein, in combination with the knowledge of one of ordinary skill in the art.

The invention claimed is:

1. An in vitro method for determining the modulating effect of a test compound on the epithelial barrier function, the method comprising the steps of
    a) providing a microfluidic system comprising multiple hollow microfluidic channels, wherein at least one microfluidic channel is filled at least in part with a hydrogel;
    b) introducing epithelial cells into the microfluidic channels and allowing the epithelial cells to contact the hydrogel;
    c) culturing the epithelial cells that were introduced into the microfluidic channels, such that the epithelial cells form directly on the hydrogel a layer of epithelial cells with an apical and a basolateral side wherein the layer of epithelial cells is a monolayer that has epithelial barrier function, wherein the apical side is facing the microfluidic channel and the basolateral side is in contact with the hydrogel;
    d) introducing a probe and a test compound to the apical side, to the basolateral side or to both the apical and basolateral side of the monolayer of epithelial cells that has epithelial barrier function, and wherein the test compound is introduced to the cells either before, after or at the same time with the probe;
    e) determining at least two successive time points the signal provided by the probe introduced to the apical side in the microfluidic channel or to the basolateral side in the hydrogel, or to the apical and the basolateral side in the microfluidic channel and in the hydrogel; and
    f) determining the modulating effect of the test compound on the epithelial barrier integrity using the signals determined in step e), wherein the extent of disruption or repair of barrier function is determined;
    wherein the microfluidic system is without any artificial membrane separating the hydrogel from the epithelial cells.

2. The method of claim 1 wherein the effect of the test compound on the epithelial barrier function is concurrently determined in more than one microfluidic channels comprising the monolayer of epithelial cells that has epithelial barrier function.

3. The method of claim 1 wherein after step c) or concurrently with step d) the monolayer of epithelial cell layer of cells with an apical and a basolateral side is disrupted.

4. The method of claim 1 wherein two successive time points in step e) are within 1 second-24 hours of each other.

5. The method of claim 1 wherein adjacent to the hydrogel a further channel is present that is in contact with the hydrogel, wherein said channel is not in direct contact with the microfluidic channel comprising the monolayer of epithelial cells.

6. The method of claim 5 wherein in said further channel a flow is present that removes the probe from the hydrogel.

7. The method of claim 1 wherein in step b) different types of epithelial cells are introduced in the same microfluidic channel or wherein in step b) different microfluidic channels are provided with different types of epithelial cells.

8. The method of claim 1 wherein the hydrogel is a basement membrane extract, an extracellular matrix component, collagen, collagen I, collagen IV, fibronectin, laminin, vitronectin, D-lysine, entactin, heparan sulfide proteoglycans or combinations thereof.

9. The method of claim 1 wherein the determining of the signal provided by the probe in step e) comprises measuring using an imaging device, a microscope, an automated microscope, a high content imager, a plate reader, or a multimode reader.

10. The method of claim 1, wherein the microfluidic system provides an uninterrupted optical path to the microfluidic channel and/or to the hydrogel.

11. The method of claim 1 wherein in step d) the probe is introduced to the monolayer of epithelial cells before the test compound is introduced.

12. The method of claim 1 wherein the microfluidic system comprises at least 3 microfluidic channels.

13. The method of claim 1 wherein probes of different size are introduced in step d).

14. The method of claim 1, where an overpressure is applied to the basolateral side or apical side of where the probe is introduced.

15. The method of claim 1 wherein in step c) the cells are allowed to form a tubular structure with an apical and a basolateral side.

16. The method of claim 6 wherein the determining of the signal provided by the probe in step e) in the hydrogel comprises measuring the signal in the flow present in said further channel.

17. The method of claim 13 wherein each different seized probe is labeled with a different fluorescent label.

* * * * *